(12) United States Patent
Sato et al.

US011712466B2

(10) Patent No.: US 11,712,466 B2
(45) Date of Patent: Aug. 1, 2023

(54) VACCINE COMPOSITION

(71) Applicant: TOHOKU UNIVERSITY, Sendai (JP)

(72) Inventors: Yasufumi Sato, Sendai (JP); Hironori Nakagami, Suita (JP); Hideki Tomioka, Ibaraki (JP)

(73) Assignee: TOHOKU UNIVERSITY, Sendai (JP)

( * ) Notice: Subject to any disclaimer, the term of this patent is extended or adjusted under 35 U.S.C. 154(b) by 476 days.

(21) Appl. No.: 16/642,704

(22) PCT Filed: Aug. 30, 2018

(86) PCT No.: PCT/JP2018/032276
§ 371 (c)(1),
(2) Date: Feb. 27, 2020

(87) PCT Pub. No.: WO2019/045025
PCT Pub. Date: Mar. 7, 2019

(65) Prior Publication Data
US 2020/0282033 A1   Sep. 10, 2020

(30) Foreign Application Priority Data

Aug. 31, 2017 (JP) ................................ 2017-166860

(51) Int. Cl.
| | | |
|---|---|---|
| *A61K 38/08* | (2019.01) | |
| *C07K 7/00* | (2006.01) | |
| *C07K 14/475* | (2006.01) | |
| *C07K 17/00* | (2006.01) | |
| *A61K 39/00* | (2006.01) | |
| *A61K 47/64* | (2017.01) | |
| *C07K 16/18* | (2006.01) | |

(52) U.S. Cl.
CPC .......... *A61K 39/0011* (2013.01); *A61K 47/64* (2017.08); *C07K 16/18* (2013.01)

(58) Field of Classification Search
None
See application file for complete search history.

(56) References Cited

U.S. PATENT DOCUMENTS 8,426,376 B2 *   4/2013   Sato .......................... A61P 9/10
                                                              435/6.12
2010/0256224 A1   10/2010  Sato et al.
2016/0009790 A1   1/2016   Sato

FOREIGN PATENT DOCUMENTS

| WO | WO 2006/073052 A1 | 7/2006 |
| WO | WO 2008/118258 A2 | 10/2008 |
| WO | WO 2014/087810 A1 | 6/2014 |

OTHER PUBLICATIONS

Koyanagi et al., "Targeting human vasohibin-2 by a neutralizing monoclonal antibody for anti-cancer treatment," *Cancer Sci.*, 108(3): 512-519 (2017).
Lee et al., "Development of a novel and feasible antibody therapy targeting vasohibin-2," *Abstracts of the 76th Annual Meeting of the Japanese Cancer Association*, p. 286, Abstract No. P-1233 (Sep. 28, 2017).
Lee et al., "A novel and feasible antibody-based medicine for cancers targeting vasohibin-2," *Programs and Abstracts of the Academic Conference of the Japanese Association for Molecular Target Therapy of Cancer*, p. 69, Abstract No. WI-4 (Apr. 16, 2018).
Miyazaki et al., "A New Strategy for the Treatment of Prostate Cancer by Targeting Vasohibin-2," *J. Urology*, 195(4S): e1148, Abstract MP90-09 (2016).
Sun et al., "Generation and characterization of rabbit polyclonal antibodies against Vasohibin-2 for determination of its intracellular localization," *Int. J. Oncol.*, 43(1): 255-261 (2013).
Tu et al., "Vasohibin 2 reduces chemosensitivity to gemcitabine in pancreatic cancer cells via Jun proto-oncogene dependent transactivation of ribonucleotide reductase regulatory subunit M2," *Mol. Cancer*, 16: 66 (2017).
Japanese Patent Office, International Search Report in International Patent Application No. PCT/JP2018/032276 (dated Oct. 30, 2018).
Cusabio, "Rabbit anti-*Homo sapiens* (Human) VASH2 Polyclonal antibody," Code CSB-PA769783EA01 Hu (Dec. 12, 2007) [available at: https://www.cusabio.com/Polyclonal-AntibodyA/ASH2-Antibody-11082549.html].
Shibuya et al., "Isolation and Characterization of Vasohibin-2 as a Homologue of VEGF-Inducible Endothelium-Derived Angiogenesis Inhibitor Vasohibin," *Arterioscler. Thromb. Vasc. Biol.*, 26(5): 1051-1057 (2006).
Sonoda et al., "Multiple processing forms and their biological activities of a novel angiogenesis inhibitor vasohibin," *Biochem. Biophys. Res. Commun.*, 342(2): 640-646 (2006).
European Patent Office, Extended European Search Report in European Patent Application No. 18849767 (dated Apr. 9, 2021).

* cited by examiner

*Primary Examiner* — Christine J Saoud
*Assistant Examiner* — Jon M Lockard
(74) *Attorney, Agent, or Firm* — Leydig, Voit & Mayer, Ltd.

(57) ABSTRACT

The present invention provides a vaccine composition for treating or preventing cancer expressing VASH2, containing a peptide including an amino acid sequence represented by SEQ ID NO: 4.

12 Claims, 18 Drawing Sheets
Specification includes a Sequence Listing.

Fig. 1

```
                   (SEQ ID NO:4)
hVASH2    1'       MTGSAADTH RCPHPKGAKG TRSRSSHARP VSLATSGGSE EEDKDGGVLF
                   *.....    *.*.       .         .           *..****..* hVASH1    1"       MPGGKKVAGG GSSGATPTSA AATAPSGVRR LETSEGTSAQ RDEEPEEEGE EDLRDGGVPF

50'       HVNKSGFPID SHTWERMWMH VAKVHPKGGE MVGAIRNAAF LAKPSIPQVP NYRLSMTIPD
                   *.*..*.*.*   ******. .*.**.*..* **.*.      *.*.**.**  .... *..*.

61"       FVNRGGLPVD EATWERMWKH VAKIHPDGEK VAQRIRGATD LPKIPIPSVP TFQPSTPVPE

110'       WLQAIQNYMK TLQYNHTGTQ FFEIRKMRPL SGLMETAKEM TRESLPIKCL EAVILGIYLT
                   .*.**.*..* .*.******* ****.*..**   *..**.*** ** *.****  **********

121"       RLEAVQRYIR ELQYNHTGTQ FFEIKKSRPL TGLMDLAKEM TKEALPIKCL EAVILGIYLT

170'       NGQPSIERFP ISFKTYFSGN YFHHVVLGIY CNGRYGSLGM SRRAELMDKP LTFRTLSDLI
                   *.*  *.*** ********** **.*.*.*.*  ****.****   ****.*.**   ** **..*.

181"       NSMPTLEREP ISFKTYFSGN YFRHIVLGVN FAGRYGALGM SRREDLMYKP PAFRTLSELV

230'       FDFEDSYKKY LHTVKKVKIG LYVPHEPHSF QPIEWKQLVL NVSKMLRADI RKELEKYARD
                   .***. ***. ..****.*.   *.**.*  .   ****. *.    *.  *.*.   ***** .**.

241"       LDFEAAYGRC WHVLKKVKLG QSVSHDPHSV EQIEWKHSVL DVERLGRDDF RKELERHARD

290'       MRMKILKPAS AHSPTQVRSR GKSLSHRRRQ ASPPRRLGRR EKSPALPEKK VADLSTLNEV
                                                         (SEQ ID NO:5)
                   **.*..*.   .***.  .*.    *** *. .**.. .     * .* .**   .. ..  .

301"       MRLKIGKGTG PPSPTKDRKK DVS-SPQRAQ SSPHRRNSRS ERRPS-GDKK TSEPKAMPDL

350'       -GYQIRI   (SEQ ID NO:1)
                    ***** .

359"       NGYQIRV   (SEQ ID NO:2)
```

Fig. 2

```
mVASH2   1'  MTGSAADTHR CPHPKITKGT RSRSSHARPV SLATSGGSEE EDKDGGVLFH VNKSGFPIDS
             ********** ***** .*** ********** ********** ********** **********
hVASH2   1"  MTGSAADTHR CPHPKGAKGT RSRSSHARPV SLATSGGSEE EDKDGGVLFH VNKSGFPIDS
             (SEQ ID NO:4)

61'  HTWERMWLHV AKVHPRGGEM VGAIRNAAFL AKPSIPQVPN YRLSMTIPDW LQAIQNYMKT
             ***** .*** ********** ********** ********** ********** **********
        61"  HTWERMWMHV AKVHPKGGEM VGAIRNAAFL AKPSIPQVPN YRLSMTIPDW LQAIQNYMKT

121'  LQYNHTGTQF FEIRKMRPLS GLMETAKEMT RESLPIKCLE AVILGIYLTN GQPSIERFPI
             ********** ********** ********** ********** ********** **********
       121"  LQYNHTGTQF FEIRKMRPLS GLMETAKEMT RESLPIKCLE AVILGIYLTN GQPSIERFPI

181'  SFKTYFSGNY FHHVVLGIYC NGYYGSLGMS RRAELMDKPL TFRTLSDLVF DFEDSYKKYL
             ********** ********** ** ******* ********** ********** *******,**
       181"  SFKTYFSGNY FHHVVLGIYC NGRYGSLGMS RRAELMDKPL TFRTLSDLIF DFEDSYKKYL

241'  HTVKKVKIGL YVPHEPHSFQ PIEWKQLVLN VSKMLRADIR KELEKYARDM RMKILKPASA
             ********** ********** ********** ********** ********** **********
       241"  HTVKKVKIGL YVPHEPHSFQ PIEWKQLVLN VSKMLRADIR KELEKYARDM RMKILKPASA

301'  HSPTQVRSRG KSLSPRRRQA SPPRRLGRRD KSPALTEKKV ADLGTLNEVG YQIRI (SEQ ID NO:3)
             ********** ***** **** ***** . *** ***** .*** *** .***** **  **
       301"  HSPTQVRSRG KSLSERRRQA SPPRRLGRRE KSPALPEKKV ADLSTLNEVG YQIRI (SEQ ID NO:1)
                        (SEQ ID NO:5)
```

Lewis lung cancer cells

B16F1 melanoma cells

Experiment plan for VASH004K (KLH conjugated antigen)

Immunize mice (C57BL6/J, Male, 8weeks old) with VASH004K peptide (a) Peptide Elisa (b) VASH2 Elisa (a)

| 29-JUL | KLH | Dead | Day | MTG | Dead | Day |
|---|---|---|---|---|---|---|
| | #127 (B:170724) | 180207 | 198 | #130 (B:170724) | 180709 | 350 |
| | #128 (B:170724) | 180320 | 239 | #137 (B:170724) | 180322 | 241 |
| | #157 (B:170810) | 180328 | 230 | #155 (B:170810) | 180212 | 186 |
| | #153 (B:170810) | 180601 | 295 | #184 (B:170810) | | 353 |
| | #183 (B:170810) | 180409 | 242 | #192 (B:170901) | 180111 | 132 |
| | #191 (B:170901) | 180515 | 256 | #225 (B:171110) | 180221 | 103 |
| | #235 (B:171201) | 180515 | 165 | #246 (B:171215) | | 226 |
| | | | | #256 (B:180104) | | 206 |

(b)

US 11,712,466 B2

SEQUENCE LISTING

```
<160> NUMBER OF SEQ ID NOS: 14

<210> SEQ ID NO 1
<211> LENGTH: 354
<212> TYPE: PRT
<213> ORGANISM: Homo sapiens

<400> SEQUENCE: 1

Met Thr Gly Ser Ala Ala Asp Thr His Arg Cys Pro His Pro Lys Gly
1               5                   10                  15

Ala Lys Gly Thr Arg Ser Arg Ser Ser His Ala Arg Pro Val Ser Leu
            20                  25                  30

Ala Thr Ser Gly Gly Ser Glu Glu Glu Asp Lys Asp Gly Gly Val Leu
        35                  40                  45

Phe His Val Asn Lys Ser Gly Phe Pro Ile Asp Ser His Thr Trp Glu
    50                  55                  60

Arg Met Trp Met His Val Ala Lys Val His Pro Lys Gly Gly Glu Met
65                  70                  75                  80

Val Gly Ala Ile Arg Asn Ala Ala Phe Leu Ala Lys Pro Ser Ile Pro
                85                  90                  95

Gln Val Pro Asn Tyr Arg Leu Ser Met Thr Ile Pro Asp Trp Leu Gln
            100                 105                 110

Ala Ile Gln Asn Tyr Met Lys Thr Leu Gln Tyr Asn His Thr Gly Thr
        115                 120                 125

Gln Phe Phe Glu Ile Arg Lys Met Arg Pro Leu Ser Gly Leu Met Glu
    130                 135                 140

Thr Ala Lys Glu Met Thr Arg Glu Ser Leu Pro Ile Lys Cys Leu Glu
145                 150                 155                 160

Ala Val Ile Leu Gly Ile Tyr Leu Thr Asn Gly Gln Pro Ser Ile Glu
                165                 170                 175

Arg Phe Pro Ile Ser Phe Lys Thr Tyr Phe Ser Gly Asn Tyr Phe His
            180                 185                 190

His Val Val Leu Gly Ile Tyr Cys Asn Gly Arg Tyr Gly Ser Leu Gly
        195                 200                 205

Met Ser Arg Arg Ala Glu Leu Met Asp Lys Pro Leu Thr Phe Arg Thr
    210                 215                 220

Leu Ser Asp Leu Ile Phe Asp Phe Glu Asp Ser Tyr Lys Lys Tyr Leu
225                 230                 235                 240
```

```
His Thr Val Lys Lys Val Lys Ile Gly Leu Tyr Val Pro His Glu Pro
                245                 250                 255

His Ser Phe Gln Pro Ile Glu Trp Lys Gln Leu Val Leu Asn Val Ser
            260                 265                 270

Lys Met Leu Arg Ala Asp Ile Arg Lys Glu Leu Glu Lys Tyr Ala Arg
            275                 280                 285

Asp Met Arg Met Lys Ile Leu Lys Pro Ala Ser Ala His Ser Pro Thr
            290                 295                 300

Gln Val Arg Ser Arg Gly Lys Ser Leu Ser Pro Arg Arg Gln Ala
305                 310                 315                 320

Ser Pro Pro Arg Arg Leu Gly Arg Arg Glu Lys Ser Pro Ala Leu Pro
                325                 330                 335

Glu Lys Lys Val Ala Asp Leu Ser Thr Leu Asn Glu Val Gly Tyr Gln
            340                 345                 350

Ile Arg

<210> SEQ ID NO 2
<211> LENGTH: 365
<212> TYPE: PRT
<213> ORGANISM: Homo sapiens

<400> SEQUENCE: 2

Met Pro Gly Gly Lys Lys Val Ala Gly Gly Ser Ser Gly Ala Thr
1               5                   10                  15

Pro Thr Ser Ala Ala Thr Ala Pro Ser Gly Val Arg Arg Leu Glu
                20                  25                  30

Thr Ser Glu Gly Thr Ser Ala Gln Arg Asp Glu Pro Glu Glu Glu
            35                  40                  45

Gly Glu Glu Asp Leu Arg Asp Gly Gly Val Pro Phe Phe Val Asn Arg
50                  55                  60

Gly Gly Leu Pro Val Asp Glu Ala Thr Trp Glu Arg Met Trp Lys His
65                  70                  75                  80

Val Ala Lys Ile His Pro Asp Gly Glu Lys Val Ala Gln Arg Ile Arg
                85                  90                  95

Gly Ala Thr Asp Leu Pro Lys Ile Pro Ile Pro Ser Val Pro Thr Phe
            100                 105                 110

Gln Pro Ser Thr Pro Val Pro Glu Arg Leu Glu Ala Val Gln Arg Tyr
            115                 120                 125

Ile Arg Glu Leu Gln Tyr Asn His Thr Gly Thr Gln Phe Phe Glu Ile
130                 135                 140

Lys Lys Ser Arg Pro Leu Thr Gly Leu Met Asp Leu Ala Lys Glu Met
145                 150                 155                 160

Thr Lys Glu Ala Leu Pro Ile Lys Cys Leu Glu Ala Val Ile Leu Gly
                165                 170                 175

Ile Tyr Leu Thr Asn Ser Met Pro Thr Leu Glu Arg Phe Pro Ile Ser
            180                 185                 190

Phe Lys Thr Tyr Phe Ser Gly Asn Tyr Phe Arg His Ile Val Leu Gly
            195                 200                 205

Val Asn Phe Ala Gly Arg Tyr Gly Ala Leu Gly Met Ser Arg Arg Glu
210                 215                 220

Asp Leu Met Tyr Lys Pro Pro Ala Phe Arg Thr Leu Ser Glu Leu Val
225                 230                 235                 240

Leu Asp Phe Glu Ala Ala Tyr Gly Arg Cys Trp His Val Leu Lys Lys
                245                 250                 255
```

-continued

Val Lys Leu Gly Gln Ser Val Ser His Asp Pro His Ser Val Glu Gln
            260                 265                 270

Ile Glu Trp Lys His Ser Val Leu Asp Val Glu Arg Leu Gly Arg Asp
        275                 280                 285

Asp Phe Arg Lys Glu Leu Glu Arg His Ala Arg Asp Met Arg Leu Lys
    290                 295                 300

Ile Gly Lys Gly Thr Gly Pro Pro Ser Pro Thr Lys Asp Arg Lys Lys
305                 310                 315                 320

Asp Val Ser Ser Pro Gln Arg Ala Gln Ser Ser Pro His Arg Arg Asn
                325                 330                 335

Ser Arg Ser Glu Arg Arg Pro Ser Gly Asp Lys Lys Thr Ser Glu Pro
            340                 345                 350

Lys Ala Met Pro Asp Leu Asn Gly Tyr Gln Ile Arg Val
        355                 360                 365

<210> SEQ ID NO 3
<211> LENGTH: 355
<212> TYPE: PRT
<213> ORGANISM: Mus musculus

<400> SEQUENCE: 3

Met Thr Gly Ser Ala Ala Asp Thr His Arg Cys Pro His Pro Lys Ile
1               5                   10                  15

Thr Lys Gly Thr Arg Ser Arg Ser Ser His Ala Arg Pro Val Ser Leu
            20                  25                  30

Ala Thr Ser Gly Gly Ser Glu Glu Glu Asp Lys Asp Gly Gly Val Leu
        35                  40                  45

Phe His Val Asn Lys Ser Gly Phe Pro Ile Asp Ser His Thr Trp Glu
    50                  55                  60

Arg Met Trp Leu His Val Ala Lys Val His Pro Arg Gly Gly Glu Met
65                  70                  75                  80

Val Gly Ala Ile Arg Asn Ala Ala Phe Leu Ala Lys Pro Ser Ile Pro
                85                  90                  95

Gln Val Pro Asn Tyr Arg Leu Ser Met Thr Ile Pro Asp Trp Leu Gln
            100                 105                 110

Ala Ile Gln Asn Tyr Met Lys Thr Leu Gln Tyr Asn His Thr Gly Thr
        115                 120                 125

Gln Phe Phe Glu Ile Arg Lys Met Arg Pro Leu Ser Gly Leu Met Glu
    130                 135                 140

Thr Ala Lys Glu Met Thr Arg Glu Ser Leu Pro Ile Lys Cys Leu Glu
145                 150                 155                 160

Ala Val Ile Leu Gly Ile Tyr Leu Thr Asn Gly Gln Pro Ser Ile Glu
                165                 170                 175

Arg Phe Pro Ile Ser Phe Lys Thr Tyr Phe Ser Gly Asn Tyr Phe His
            180                 185                 190

His Val Val Leu Gly Ile Tyr Cys Asn Gly Tyr Tyr Gly Ser Leu Gly
        195                 200                 205

Met Ser Arg Arg Ala Glu Leu Met Asp Lys Pro Leu Thr Phe Arg Thr
    210                 215                 220

Leu Ser Asp Leu Val Phe Asp Phe Glu Asp Ser Tyr Lys Lys Tyr Leu
225                 230                 235                 240

His Thr Val Lys Lys Val Lys Ile Gly Leu Tyr Val Pro His Glu Pro
                245                 250                 255

His Ser Phe Gln Pro Ile Glu Trp Lys Gln Leu Val Leu Asn Val Ser
            260                 265                 270

```
Lys Met Leu Arg Ala Asp Ile Arg Lys Glu Leu Glu Lys Tyr Ala Arg
        275                 280                 285

Asp Met Arg Met Lys Ile Leu Lys Pro Ala Ser Ala His Ser Pro Thr
    290                 295                 300

Gln Val Arg Ser Arg Gly Lys Ser Leu Ser Pro Arg Arg Gln Ala
305                 310                 315                 320

Ser Pro Pro Arg Arg Leu Gly Arg Arg Asp Lys Ser Pro Ala Leu Thr
                325                 330                 335

Glu Lys Lys Val Ala Asp Leu Gly Thr Leu Asn Glu Val Gly Tyr Gln
            340                 345                 350

Ile Arg Ile
        355
```

```
<210> SEQ ID NO 4
<211> LENGTH: 10
<212> TYPE: PRT
<213> ORGANISM: Artificial Sequence
<220> FEATURE:
<223> OTHER INFORMATION: Synthetic Sequence - MTG(peptide derived from
      hVASH-2)

<400> SEQUENCE: 4

Met Thr Gly Ser Ala Ala Asp Thr His Arg
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Sequence - RRR(peptide derived from
      hVASH-2)

<400> SEQUENCE: 5

Arg Arg Arg Gln Ala Ser Pro Pro Arg Arg
1               5                   10

<210> SEQ ID NO 6
<211> LENGTH: 21
<212> TYPE: DNA
<213> ORGANISM: Artificial Sequence
<220> FEATURE:
<223> OTHER INFORMATION: Primer Sequence

<400> SEQUENCE: 6
ttcagcgaga tcctgagggt c                                            21

<210> SEQ ID NO 7
<211> LENGTH: 21
<212> TYPE: DNA
<213> ORGANISM: Artificial Sequence
<220> FEATURE:
<223> OTHER INFORMATION: Primer sequence

<400> SEQUENCE: 7
cgcttgggtg tcattcacga c                                            21

<210> SEQ ID NO 8
<211> LENGTH: 20
<212> TYPE: DNA
<213> ORGANISM: Artificial Sequence
<220> FEATURE:
<223> OTHER INFORMATION: Primer sequence
```

<400> SEQUENCE: 8
gccaggtaca tcgacttcct                                               20

<210> SEQ ID NO 9
<211> LENGTH: 19
<212> TYPE: DNA
<213> ORGANISM: Artificial Sequence
<220> FEATURE:
<223> OTHER INFORMATION: Primer sequence

<400> SEQUENCE: 9
ccagacggag aaggcgtag                                                19

<210> SEQ ID NO 10
<211> LENGTH: 20
<212> TYPE: DNA
<213> ORGANISM: Artificial Sequence
<220> FEATURE:
<223> OTHER INFORMATION: Primer sequence

<400> SEQUENCE: 10
gaggacagtg gcaaaagctc                                               20

<210> SEQ ID NO 11
<211> LENGTH: 19
<212> TYPE: DNA
<213> ORGANISM: Artificial Sequence
<220> FEATURE:
<223> OTHER INFORMATION: Primer sequence

<400> SEQUENCE: 11
cagctgcttg ggaagttgg                                                19

<210> SEQ ID NO 12
<211> LENGTH: 20
<212> TYPE: DNA
<213> ORGANISM: Artificial Sequence
<220> FEATURE:
<223> OTHER INFORMATION: Primer sequence

<400> SEQUENCE: 12
ctcccagtca gccaccttta                                               20

<210> SEQ ID NO 13
<211> LENGTH: 20
<212> TYPE: DNA
<213> ORGANISM: Artificial Sequence
<220> FEATURE:
<223> OTHER INFORMATION: Primer sequence

<400> SEQUENCE: 13
ggttcacaga atcggcgatc                                               20

<210> SEQ ID NO 14
<211> LENGTH: 20
<212> TYPE: PRT
<213> ORGANISM: Artificial Sequence
<220> FEATURE:
<223> OTHER INFORMATION: Synthetic Sequence - OSK-1 peptide

```
<400> SEQUENCE: 14

Glu Leu Lys Leu Ile Phe Leu His Arg Leu Lys Arg Leu Arg Lys Arg
1               5                   10                  15

Leu Lys Arg Lys
            20
```

VACCINE COMPOSITION

CROSS-REFERENCE TO RELATED APPLICATIONS

This patent application is the U.S. national phase of International Patent Application No. PCT/JP2018/032276, filed Aug. 30, 2018, which claims the benefit of Japanese Patent Application No. 2017-166860, filed on Aug. 31, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 11,906 bytes ASCII (Text) file named "748321SequenceListing.txt," created Feb. 27, 2020.

TECHNICAL FIELD

The present invention relates to a vaccine composition. In particular, the present invention relates to a vaccine composition containing a peptide derived from a vasohibin-2 protein for treating or preventing cancer, and the like.

BACKGROUND ART

In general, tumor growth is limited to 1 to 2 mm$^3$ when new blood vessels are not formed and blood is not supplied, and angiogenesis is considered to have a critical role in tumor growth, invasion and metastasis. It has also been demonstrated that inhibition of tumor angiogenesis is associated with inhibition of tumor progression.

In order to achieve inhibition of angiogenesis, many researchers have studied vascular endothelial growth factors (VEGF) that plays a crucial role in regulating the process of angiogenesis, and VEGF receptors (VEGFR).

The present inventors have isolated and identified a novel angiogenesis inhibitory factor vasohibin-1 (VASH1) that is considered to function as a negative feedback regulatory factor of angiogenesis whose expression is induced in vascular endothelial cells by stimulation with VEGF and its homolog vasohibin-2 (VASH2). It has been known that both VASH1 and VASH2 are efficiently secreted extracellularly by binding to a small vasohibin binding protein (SVBP) in cells and express their actions.

VASH1 has a broad-spectrum inhibitory activity not only against angiogenesis but also against lymphangiogenesis, and VASH1 is the first endogenous factor having such an activity. In particular, since angiogenesis is directly linked to cancer growth and distant metastasis, and lymphangiogenesis is directly linked to lymph node metastasis, application of VASH1 to cancer treatment is expected.

In contrast, VASH2 is a factor that promotes angiogenesis by competing with VASH1. It has been known that in the observation in an angiogenesis model, VASH1 is mainly expressed in vascular endothelial cells posterior to the sprouting area to terminate angiogenesis, whereas VASH2 is mainly expressed in bone marrow-derived CD11b-positive monocytes that infiltrate into the sprouting area where angiogenesis is active to promote angiogenesis at the sprouting site.

Moreover, it has also been observed that not only monocytes that infiltrate into the stroma, but also cancer cells express VASH2 in cancer tissue, and promote tumor growth via tumor angiogenesis, and further act on cancer cells themselves, so that epithelial-mesenchymal transition or drug resistance may be enhanced.

In view of such a circumstance, the present inventors have reported a pharmaceutical composition for treatment of a disease requiring inhibition of angiogenesis, which contains an anti-VASH2 antibody, and the like (PTL 1).

CITATION LIST

Patent Literature

PTL 1: WO 2014/087810

SUMMARY OF INVENTION

Technical Problem

An object of the present invention is to provide a method for treating or preventing cancer through an approach different from conventional anticancer agents by focusing on the biological action of VASH2.

Solution to Problem

As a result of intensive studies to achieve the above object, the present inventors found that (1) a peptide including an amino acid sequence represented by SEQ ID NO: 4 can induce the production of an antibody blocking VASH2 actoin, (2) in an animal model immunized with the peptide, tumorigenesis is inhibited and the expression of an angiogenesis marker is decreased, and in addition, the expression of an epithelial-mesenchymal transition marker is inhibited, (3) serum derived from an individual whose antibody titer has increased by immunization using the peptide has a migration inhibitory effect on cancer cells, and (4) in an individual whose antibody titer has increased by immunization using the peptide, cancer cell metastasis is prevented. The present invention is completed by further studies conducted as follows.

[1] A vaccine composition for treating or preventing cancer expressing VASH2 containing either or both of:
(1) a peptide including an amino acid sequence represented by SEQ ID NO: 4; and
(2) a peptide including an amino acid sequence represented by SEQ ID NO: 4 conjugated with a carrier protein.

[2] A vaccine composition for inhibiting metastasis of cancer expressing VASH2, containing either or both of:
(1) a peptide including an amino acid sequence represented by SEQ ID NO: 4; and
(2) a peptide including an amino acid sequence represented by SEQ ID NO: 4 conjugated with a carrier protein.

[3] The vaccine composition according to [1] or [2], wherein the peptide is amidated at the C-terminus.

[4] The vaccine composition according to any one of [1] to [3], wherein the carrier protein is selected from the group consisting of bovine serum albumin (BSA), rabbit serum albumin (RSA), ovalbumin (OVA), keyhole limpet hemocyanin (KLH), OSK-1, thyroglobulin (TG), and an immunoglobulin.

[5] The vaccine composition according to any one of [1] to [4], wherein the cancer expressing VASH2 is selected from the group consisting of pancreatic cancer, ovarian cancer, bile duct cancer, esophageal cancer, stomach cancer, colon cancer, liver cancer, gallbladder cancer, breast cancer, oral cancer, cervical cancer, endometrial cancer, renal cell cancer, bladder cancer, prostate cancer, a testicular tumor, lung cancer, skin cancer, and a brain tumor.

[6] A method for treating or preventing cancer expressing VASH2, including administering either or both of:
(1) a peptide including an amino acid sequence represented by SEQ ID NO: 4; and
(2) a peptide including an amino acid sequence represented by SEQ ID NO: 4 conjugated with a carrier protein;
to a subject.

[7] A method for inhibiting metastasis of cancer expressing VASH2, including administering either or both of:
(1) a peptide including an amino acid sequence represented by SEQ ID NO: 4; and
(2) a peptide including an amino acid sequence represented by SEQ ID NO: 4 conjugated with a carrier protein;
to a subject.

[8] The method according to [6] or [7], wherein the peptide is amidated at the C-terminus.

[9] The method according to any one of [6] to [8], wherein the carrier protein is selected from the group consisting of bovine serum albumin (BSA), rabbit serum albumin (RSA), ovalbumin (OVA), keyhole limpet hemocyanin (KLH), OSK-1, thyroglobulin (TG), and an immunoglobulin.

[10] The method according to any one of [5] to [9], wherein the cancer expressing VASH2 is selected from the group consisting of pancreatic cancer, ovarian cancer, bile duct cancer, esophageal cancer, stomach cancer, colon cancer, liver cancer, gallbladder cancer, breast cancer, oral cancer, cervical cancer, endometrial cancer, renal cell cancer, bladder cancer, prostate cancer, a testicular tumor, lung cancer, skin cancer, and a brain tumor.

[11] An antibody against VASH2 or an immunologically active fragment thereof that specifically recognizes an amino acid sequence represented by SEQ ID NO: 4.

[12] A peptide including an amino acid sequence represented by SEQ ID NO: 4.

[13] (1) A peptide including an amino acid sequence represented by SEQ ID NO: 4; and/or (2) a peptide including an amino acid sequence represented by SEQ ID NO: 4 conjugated with a carrier protein for use in treatment or prevention of cancer expressing vasohibin-2 (VASH2).

[14] (1) A peptide including an amino acid sequence represented by SEQ ID NO: 4; and/or
(2) a peptide including an amino acid sequence represented by SEQ ID NO: 4 conjugated with a carrier protein for use in inhibition of metastasis of cancer expressing VASH2.

[15] The peptide according to [13] or [14], wherein the peptide is amidated at the C-terminus.

[16] The peptide according to any one of [13] to [15], wherein the carrier protein is selected from the group consisting of bovine serum albumin (BSA), rabbit serum albumin (RSA), ovalbumin (OVA), keyhole limpet hemocyanin (KLH), OSK-1, thyroglobulin (TG), and an immunoglobulin.

[17] The peptide according to any one of [13] to [16], wherein the cancer expressing VASH2 is selected from the group consisting of pancreatic cancer, ovarian cancer, bile duct cancer, esophageal cancer, stomach cancer, colon cancer, liver cancer, gallbladder cancer, breast cancer, oral cancer, cervical cancer, endometrial cancer, renal cell cancer, bladder cancer, prostate cancer, a testicular tumor, lung cancer, skin cancer, and a brain tumor.

[18] Use of
(1) a peptide including an amino acid sequence represented by SEQ ID NO: 4; and/or
(2) a peptide including an amino acid sequence represented by SEQ ID NO: 4 conjugated with a carrier protein for producing a vaccine composition for treating or preventing cancer expressing vasohibin-2 (VASH2).

[19] Use of
(1) a peptide including an amino acid sequence represented by SEQ ID NO: 4; and/or
(2) a peptide including an amino acid sequence represented by SEQ ID NO: 4 conjugated with a carrier protein for producing a vaccine composition for inhibiting metastasis of cancer expressing VASH2.

[20] The Use according to [18] or [19], wherein the peptide is amidated at the C-terminus.

[21] The Use according to any one of [18] to [20], wherein the carrier protein is selected from the group consisting of bovine serum albumin (BSA), rabbit serum albumin (RSA), ovalbumin (OVA), keyhole limpet hemocyanin (KLH), OSK-1, thyroglobulin (TG), and an immunoglobulin.

[22] The Use according to any one of [18] to [21], wherein the cancer expressing VASH2 is selected from the group consisting of pancreatic cancer, ovarian cancer, bile duct cancer, esophageal cancer, stomach cancer, colon cancer, liver cancer, gallbladder cancer, breast cancer, oral cancer, cervical cancer, endometrial cancer, renal cell cancer, bladder cancer, prostate cancer, a testicular tumor, lung cancer, skin cancer, and a brain tumor.

Advantageous Effects of Invention

According to the present invention, by administering the vaccine composition of the present invention to a subject that has cancer expressing VASH2, the subject having VASH2 expressing cancer can be treated. Further, according to the present invention, by administering the vaccine composition of the present invention to a subject that may develop cancer expressing VASH2, the development of the cancer can be prevented. Further, according to the present invention, by administering the vaccine composition of the present invention to a subject that had cancer expressing VASH2 before, recurrence of the cancer can be prevented. In addition, according to the present invention, by administering the vaccine composition of the present invention to a subject that has cancer expressing VASH2, metastasis of the cancer can be inhibited. Further, by using an antibody that recognizes a partial amino acid sequence of VASH2 represented by SEQ ID NO: 4, the above-mentioned effects can be obtained.

BRIEF DESCRIPTION OF DRAWINGS

FIG. 2 is a diagram showing homology between human VASH2 (SEQ ID NO: 1) and mouse VASH2 (SEQ ID NO: 3). Human VASH2 and mouse VASH2 show high homology, and the sequences of both in regions corresponding to two types of peptides (SEQ ID NOS: 4 and 5) used for inducing production of an antibody are identical.

FIG. 11(a) shows the antibody titer against an antigen peptide, and FIG. 11(b) shows the antibody titer against a recombinant human VASH2 protein.

FIG. 14(a) shows the date of death (Dead) and the number of days alive (Day) of each mouse. In the table, #157, #183, #184, and #246 are female mice, and the others are male mice. In the case where the column of "Dead" is blank, it indicates that the mouse is alive. The numerical value given in the column of "Day" of a living mouse denotes the number of days alive as of Jul. 29, 2018, and may further increase. FIG. 14(b) shows the survival curves of the KPC mice to which MTG peptide vaccine or KLH was administered.

FIG. 17-1 is a view showing antibody titers at 28 days after administration of vaccine (day 28) in C57BL/6Jx129SVJ mice (n=11) to which MTG peptide vaccine was administered.

FIG. 17-2 is a view showing tumor sizes at 7 to 15 days after implantation of K5 cells in C57BL/6Jx129SVJ mice (n=11) to which MTG peptide vaccine was administered.

DESCRIPTION OF EMBODIMENTS

Figure 3:
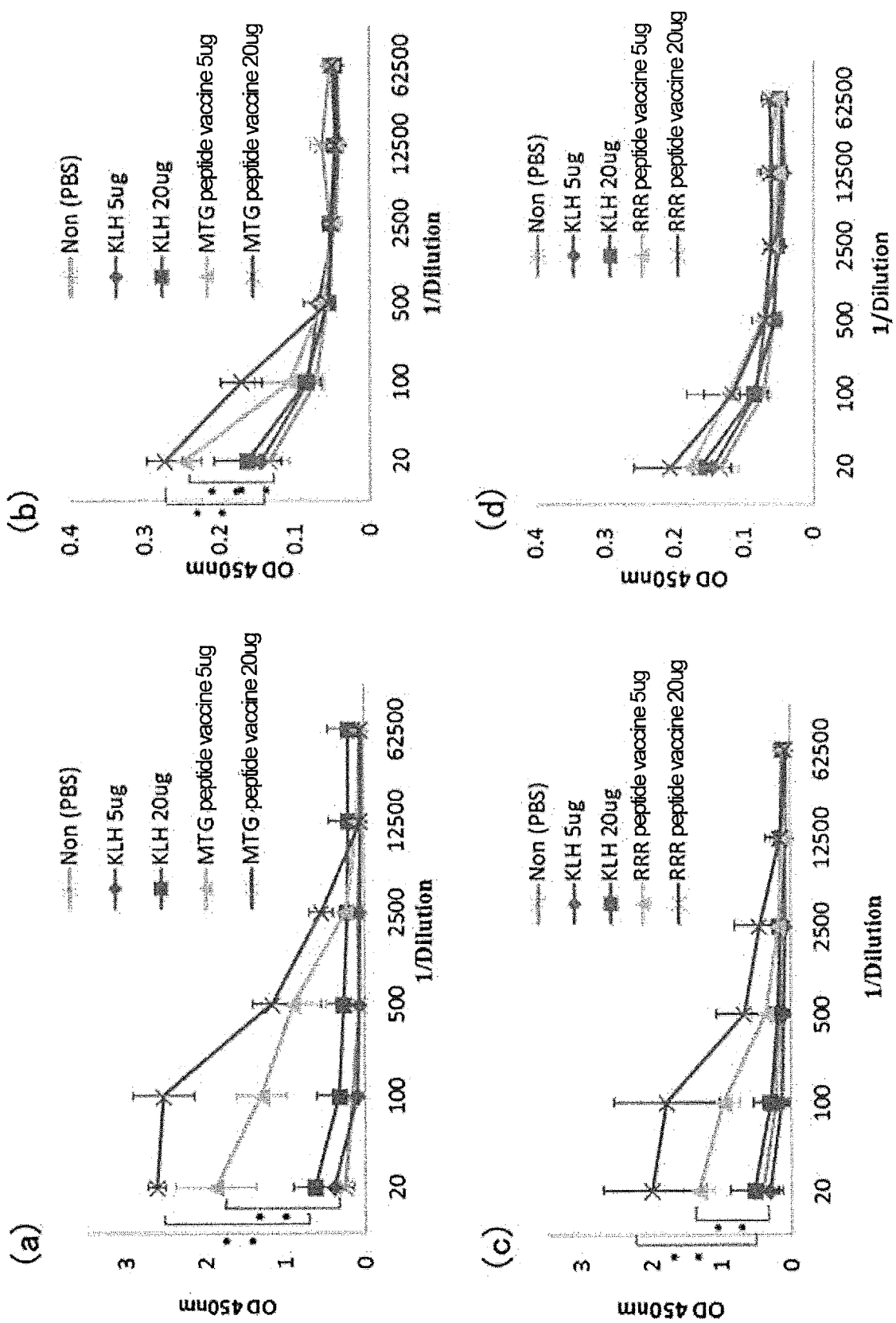
FIG. 3 is a view showing results of verifying an increase in the antibody titer in the blood of mice immunized with two types of peptide vaccines (MTG peptide vaccine and RRR peptide vaccine) using ELISA. In either case of MTG and RRR, a significant concentration-dependent increase in the antibody titer against the antigen peptide was observed (FIGS. 3(a) and 3(c)). On the other hand, against a recombinant human VASH2 protein, a significant increase in the antibody titer was observed only in the mice immunized with the MTG peptide vaccine but not in the mice immunized with the RRR peptide vaccine (FIGS. 3(b) and 3(d)).

Hereinafter, the present invention will be described in detail.

1. Vaccine Composition

The present invention provides a vaccine composition for treating or preventing cancer expressing vasohibin-2 (VASH2) containing either or both of: (1) a peptide including an amino acid sequence represented by SEQ ID NO: 4; and (2) a peptide including an amino acid sequence represented by SEQ ID NO: 4 conjugated with a carrier protein. Further, the present invention provides a vaccine composition for inhibiting metastasis of cancer expressing VASH2 containing either or both of: (1) a peptide including an amino acid sequence represented by SEQ ID NO: 4; and (2) a peptide including an amino acid sequence represented by SEQ ID NO: 4 conjugated with a carrier protein. Hereinafter, these are sometimes referred to as "the vaccine composition of the present invention". In addition, the present invention provides a peptide and a peptide complex conjugated with a carrier protein, each of which is an active ingredient of the vaccine composition of the present invention. Hereinafter, these are sometimes referred to as "the peptide or the like of the present invention". Note that in the present description, the term "vaccine composition" means a biological preparation containing an antigen inducing a specific immunoreaction (production of a specific antibody). In the present invention, the vaccine can include a peptide that may be modified.

Human VASH2 is a protein composed of 355 amino acids (SEQ ID NO: 1), and its gene is encoded in 1q32.3 of a human chromosome. In the VASH2 protein, existing functional motifs and the like have not been observed, and it is difficult to deduce its function or three-dimensional structure based on the amino acid sequence by analogy at present.

It has been reported that VASH2 is expressed in inflammatory cells or cancer cells. Examples of cancer expressing VASH2 include pancreatic cancer, ovarian cancer, bile duct cancer, esophageal cancer, stomach cancer, colon cancer, liver cancer, gallbladder cancer, breast cancer, oral cancer, cervical cancer, endometrial cancer, renal cell cancer, bladder cancer, prostate cancer, a testicular tumor, lung cancer, skin cancer, and a brain tumor, but are not limited thereto. The cancer expressing VASH2 can be easily identified by those skilled in the art using a method known per se such as immunostaining or Western blotting. Although not wishing to be bound by theory, in consideration that there has been knowledge that cancer cells highly expressing VASH2 are relatively susceptible to malignant transformation, and the vaccine composition of the present invention can induce an anti-VASH2 antibody, as a more preferred subject to which the vaccine composition of the present invention is applied, a subject that has cancer highly expressing VASH2 can be exemplified. Note that the phrase "highly expressing VASH2" refers to that when the expression level of VASH2 is semiquantified into the following scores: 0: negative, 1: weakly positive, 2: moderately positive, and 3: strongly positive by comparison with the expression level of VASH2 in monocytes in cancer stroma, a score of 1 or more is defined as positive, and particularly preferably, a score of 3 is defined as high expression (for details, see Kim J C et al, Hepatogastroenterology. 2015 March-April; 62 (138): 251-6). Note that examples of the cancer highly expressing VASH2 include ovarian cancer, liver cancer, and pancreatic cancer, but are not limited thereto.

A subject to which the vaccine composition of the present invention is administered may be any mammal, but is a mammal which has cancer expressing VASH2 or a mammal which may have cancer expressing VASH2. The mammal which may have cancer expressing VASH2 includes a mammal which had cancer expressing VASH2, but is not limited thereto. Examples of the mammal include experimental animals such as mice, rats, hamsters, guinea pigs, and rabbits, pets such as dogs and cats, domestic animals such as cattle, pigs, goats, horses, and sheep, and humans, monkeys, orangutans, and chimpanzees, and particularly humans are preferred. The subject to which the composition is administered may or may not receive treatment of cancer.

The vaccine composition of the present invention can be administered orally or parenterally to a subject. In the case of oral administration, the peptide serving as the active ingredient can be degraded in the stomach, and therefore, parenteral administration is preferred. As a preferred preparation for oral administration, a liquid, a capsule, a sachet, a tablet, a suspension, an emulsion, and the like are included. As a preferred preparation for parenteral administration (for example, subcutaneous injection, intramuscular injection, local injection, intraperitoneal administration, or the like), there are aqueous and non-aqueous isotonic sterile injection solutions, and they may contain an antioxidant, a buffer solution, a bacteriostatic agent, an isotonic agent, or the like. Further, aqueous and non-aqueous sterile suspension agents are exemplified, and they may contain a suspending agent, a solubilizer, a thickener, a stabilizer, a preservative, or the like. The preparation can be enclosed in a container for each unit dose or multiple doses such as an ampoule or a vial. In addition, the active ingredient and a pharmaceutically acceptable carrier can be lyophilized and stored in a state where they may be dissolved or suspended in an appropriate sterile vehicle immediately before use.

The content of the active ingredient (1) and/or (2) in the vaccine composition is usually about 0.1 to 100 wt %, preferably about 1 to 99 wt %, and more preferably about 10 to 90 wt % of the entire vaccine composition. Note that when both (1) and (2) are contained in the vaccine composition, they may be contained in such an amount that the total amount falls within the above-mentioned range.

The dose of the vaccine composition of the present invention can vary depending on the amount of the active ingredient in the vaccine composition, the contained materials other than the active ingredient, the subject to which the composition is administered, the administration method, the dosage form, etc., however, in general, the peptide serving as the active ingredient is administered at a dose within a range of 1 μg to 1000 μg, preferably within a range of 20 μg to 100 g per adult usually two to three times over 4 weeks to 12 weeks, and when the antibody titer has decreased, one additional administration is made on each occasion. An appropriate dose or an appropriate administration method can be suitably selected by those skilled in the art.

By administering the vaccine composition of the present invention to a subject, a specific immune response (production of a specific antibody) against VASH2 is induced, the mammal acquires a neutralizing antibody against VASH2, and the function of VASH2 is inhibited. As a result, the prevention or treatment of cancer expressing VASH2 or the inhibition of metastasis of cancer cells expressing VASH2 is achieved.

The "peptide including an amino acid sequence represented by SEQ ID NO: 4" contained in the vaccine composition of the present invention can be a partial sequence of a human VASH2 protein (that is, SEQ ID NO: 1) including an amino acid sequence represented by SEQ ID NO: 4. Examples of the partial sequence of SEQ ID NO: 1 including the amino acid sequence represented by SEQ ID NO: 4 include a peptide that is a peptide composed of part or all of an amino acid sequence at positions 1 to 300 in the amino acid sequence represented by SEQ ID NO: 1 and includes the amino acid sequence represented by SEQ ID NO: 4, a peptide that is a peptide composed of part or all of an amino acid sequence at positions 1 to 200 in the amino acid sequence represented by SEQ ID NO: 1 and includes the amino acid sequence represented by SEQ ID NO: 4, a peptide that is a peptide composed of part or all of an amino acid sequence at positions 1 to 100 in the amino acid sequence represented by SEQ ID NO: 1 and includes the amino acid sequence represented by SEQ ID NO: 4, a peptide that is a peptide composed of part or all of an amino acid sequence at positions 1 to 50 in the amino acid sequence represented by SEQ ID NO: 1 and includes the amino acid sequence represented by SEQ ID NO: 4, a peptide that is a peptide composed of part or all of an amino acid sequence at positions 1 to 40 in the amino acid sequence represented by SEQ ID NO: 1 and includes the amino acid sequence represented by SEQ ID NO: 4, a peptide that is a peptide composed of part or all of an amino acid sequence at positions 1 to 30 in the amino acid sequence represented by SEQ ID NO: 1 and includes the amino acid sequence represented by SEQ ID NO: 4, a peptide that is a peptide composed of part or all of an amino acid sequence at positions 1 to 20 in the amino acid sequence represented by SEQ ID NO: 1 and includes the amino acid sequence represented by SEQ ID NO: 4, and a peptide that is a peptide composed of part or all of an amino acid sequence at positions 1 to 15 in the amino acid sequence represented by SEQ ID NO: 1 and includes the amino acid sequence represented by SEQ ID NO: 4, but are not limited thereto. Note that it may be a peptide in which one to several (preferably 1, 2, 3, 4, or 5) amino acid residues are deleted, substituted, inserted, or added in the partial sequence as long as a desired effect is obtained. The site of the mutation (deletion, substitution, insertion, or addition) is not particularly limited, and may be within the amino acid sequence represented by SEQ ID NO: 4 or within the VASH2 sequence located at the C-terminal side of the amino acid sequence, but the number of mutation sites within the amino acid sequence represented by SEQ ID NO: 4 is preferably 1 or 2.

Examples of the "substitution of an amino acid residue" include conservative amino acid substitution. The conservative amino acid substitution refers to substitution of a specific amino acid with an amino acid having a side chain with the same property as the side chain of the amino acid. Specifically, in the conservative amino acid substitution, a particular amino acid is substituted with another amino acid that belongs to the same group as the amino acid. The group of amino acids having a side chain with the same property is known in the art. Examples of such a group of amino acids include amino acids having a basic side chain (for example, lysine, arginine, and histidine), amino acids having an acidic side chain (for example, aspartic acid and glutamic acid), and amino acids having a neutral side chain (for example, glycine, asparagine, glutamine, serine, threonine, tyrosine, cysteine, alanine, valine, leucine, isoleucine, proline, phenylalanine, methionine, and tryptophan). Further, the amino acids having a neutral side chain can be further classified into amino acids having a polar side chain (for example, asparagine, glutamine, serine, threonine, tyrosine, and cysteine), and amino acids having a nonpolar side chain (for example, glycine, alanine, valine, leucine, isoleucine, proline, phenylalanine, methionine, and tryptophan). Further, as another group, for example, amino acids having an aromatic side chain (for example, phenylalanine, tryptophan, and tyrosine), amino acids having a side chain containing a hydroxy group (an alcoholic hydroxy group or a phenolic hydroxy group) (for example, serine, threonine, and tyrosine), and the like can also be exemplified.

Examples of the "deletion of an amino acid residue" include deletion of an arbitrary amino acid residue selected from the partial sequence of the human VASH2 protein (that is, SEQ ID NO: 1) including the amino acid sequence represented by SEQ ID NO: 4.

Examples of the "insertion of an amino acid residue" or the "addition of an amino acid residue" include insertion of an amino acid residue into the partial sequence of the human VASH2 protein (that is, SEQ ID NO: 1) including the amino acid sequence represented by SEQ ID NO: 4 or addition of an amino acid residue to the N-terminal side or the C-terminal side of the partial sequence.

Examples of the "addition of an amino acid residue" include addition of one to two residues of arginine (Arg) or lysine (Lys) each of which is a basic amino acid to the N-terminal side or the C-terminal side of the amino acid sequence for enhancing the water solubility of the peptide. Alternatively, for example, cysteine (Cys) may be added to the N-terminal side or the C-terminal side of the amino acid sequence for the purpose of conjugation with a carrier protein. In one aspect, the peptide including the amino acid sequence represented by SEQ ID NO: 4 can be a peptide composed of an amino acid sequence in which one to two amino acid residues are added to the N or C-terminus of the partial sequence of SEQ ID NO: 1 including the amino acid sequence represented by SEQ ID NO: 4. Alternatively, in one aspect, the peptide including the amino acid sequence represented by SEQ ID NO: 4 can be a peptide composed of an amino acid sequence in which one to two amino acid residues are added to the N or C-terminus of the peptide composed of the amino acid sequence represented by SEQ ID NO: 4.

The "peptide including the amino acid sequence represented by SEQ ID NO: 4" and the "peptide including the amino acid sequence represented by SEQ ID NO: 4 conjugated with a carrier protein" contained in the vaccine composition of the present invention may be amidated at the C-terminus. Here, the phrase "amidated at the C-terminus" specifically means that a carboxyl group (—COOH) at the C-terminus of the peptide is substituted with an amide group (—CO—NR$^1$R$^2$; R$^1$ and R$^2$ each independently represent a hydrogen atom, or an alkyl group, an aryl group, or a heterocyclic group, each of which may be substituted). Examples of a modifying group at the C-terminus of the peptide of the present invention include amide (—CONH$_2$), methylamide (—NHCH$_3$), ethylamide (—NHC$_2$Hs), paranitroanilide (-pNA), and methylcoumarinamide (-MCA), and an amide group is preferred.

Therefore, in one aspect, the vaccine composition of the present invention can be a vaccine composition for treating or preventing cancer expressing vasohibin-2 (VASH2), containing either or both of: (1) a peptide that is a peptide including an amino acid sequence represented by SEQ ID NO: 4, and the peptide being amidated at the C-terminus; and (2) a peptide that is a peptide including an amino acid sequence represented by SEQ ID NO: 4 conjugated with a carrier protein, and the peptide being amidated at the C-terminus. In addition, the vaccine composition of the present invention can be a vaccine composition for inhibiting metastasis of cancer expressing VASH2, containing either or both of: (1) a peptide that is a peptide including an amino acid sequence represented by SEQ ID NO: 4 and the peptide being amidated at the C-terminus; and (2) a peptide that is a peptide including an amino acid sequence represented by SEQ ID NO: 4 conjugated with a carrier protein, and the peptide being amidated at the C-terminus.

In a preferred aspect, the peptide contained in the vaccine composition of the present invention is "a peptide composed of an amino acid sequence represented by SEQ ID NO: 4". That is, the vaccine composition of the present invention can be a vaccine composition for treating or preventing cancer expressing vasohibin-2 (VASH2), containing either or both of: (1) a peptide composed of an amino acid sequence represented by SEQ ID NO: 4; and (2) a peptide composed of an amino acid sequence represented by SEQ ID NO: 4 conjugated with a carrier protein. In addition, the vaccine composition of the present invention can be a vaccine composition for inhibiting metastasis of cancer expressing VASH2, containing either or both of: (1) a peptide composed of an amino acid sequence represented by SEQ ID NO: 4; and (2) a peptide composed of an amino acid sequence represented by SEQ ID NO: 4 conjugated with a carrier protein.

Note that in a more preferred aspect, the vaccine composition of the present invention can be a vaccine composition for treating or preventing cancer expressing vasohibin-2 (VASH2), containing either or both of: (1) a peptide that is a peptide composed of an amino acid sequence represented by SEQ ID NO: 4, and the peptide being amidated at the C-terminus; and (2) a peptide that is a peptide composed of an amino acid sequence represented by SEQ ID NO: 4 conjugated with a carrier protein, and the peptide being amidated at the C-terminus. In addition, the vaccine composition of the present invention can be a vaccine composition for inhibiting metastasis of cancer expressing VASH2, containing either or both of: (1) a peptide that is a peptide composed of an amino acid sequence represented by SEQ ID NO: 4 and the peptide being amidated at the C-terminus; and (2) a peptide that is a peptide composed of an amino acid sequence represented by SEQ ID NO: 4 conjugated with a carrier protein, and the peptide being amidated at the C-terminus.

Further, the "peptide including an amino acid sequence represented by SEQ ID NO: 4 conjugated with a carrier protein" contained in the vaccine composition of the present invention means a peptide complex in which the "peptide including an amino acid sequence represented by SEQ ID NO: 4" is conjugated with a carrier protein for the purpose of enhancing the immunogenicity of the peptide. In a preferred aspect, the "peptide including an amino acid sequence represented by SEQ ID NO: 4 conjugated with a carrier protein" can be a peptide composed of an amino acid sequence represented by SEQ ID NO: 4 conjugated with a carrier protein. In a more preferred aspect, the "peptide including an amino acid sequence represented by SEQ ID NO: 4 conjugated with a carrier protein" can be a peptide, which is a peptide composed of an amino acid sequence represented by SEQ ID NO: 4 conjugated with a carrier protein, and in which the amino acid sequence represented by SEQ ID NO: 4 is amidated at the C-terminus.

The carrier protein is generally a substance that imparts immunogenicity to a molecule having no immunogenicity due to its small molecular weight by being bound to the molecule, and is known in the present technical field. The carrier protein used for the vaccine composition of the present invention is not particularly limited as long as a desired effect is obtained, and for example, bovine serum albumin (BSA), rabbit serum albumin (RSA), ovalbumin (OVA), keyhole limpet hemocyanin (KLH), a peptide having OSK-1 (an amino acid sequence ELKLIFLHRLKRLRKRLKRK (SEQ ID NO: 14), see WO 2016/047763 (PCT/JP2015/077139) or U.S. patent application Ser. No. 15/514,310, each of which is incorporated herein by reference), thyroglobulin (TG), an immunoglobulin, and the like are exemplified. As a preferred carrier protein, keyhole limpet hemocyanin (KLH) is exemplified.

In the formation of the complex of the peptide represented by SEQ ID NO: 4 with the carrier protein, an arbitrary known method can be applied as long as antigenicity is maintained. In order to conjugate the peptide with the carrier protein, a carbodiimide method, a glutaraldehyde method, a diazo condensation method, an MBS (maleimidobenzoyloxy succinimide) method, or the like can be used. Preferably, a glutaraldehyde method is used. Incidentally, with respect to preparation of the complex of the peptide with the carrier protein, the blending ratio of the peptide and the carrier protein can be suitably changed by the peptide, the carrier protein, or the method for forming the complex to be used, however, for example, when a peptide composed of an amino acid sequence represented by SEQ ID NO: 4 that is amidated at the C-terminus or is not amidated at the C-terminus is conjugated to KLH using a glutaraldehyde method, the ratio of the peptide to KLH is usually 10 nmol/mg of the conjugate to 300 nmol/mg of the conjugate, preferably 30 nmol/mg of the conjugate to 200 nmol/mg of the conjugate, and more preferably 50 nmol/mg of the conjugate to 150 nmol/mg of the conjugate in terms of the number of moles of the peptide per unit mass of the conjugate. Alternatively, in the formation of the complex of the peptide represented by SEQ ID NO: 4 with OSK-1 peptide, for example, by using epsilon-aminocaproic acid (ε-Acp) or the like as a spacer, the conjugation can be carried out by a method known per se (see WO 2016/047763 (PCT/JP2015/077139) or U.S. patent application Ser. No. 15/514,310)

Note that when the peptide complex is prepared using an MBS method, one to two, preferably one amino acid (for example, cysteine) may be added to the peptide of SEQ ID NO: 4. The position of the amino acid to be added is preferably the N-terminus or the C-terminus of the peptide.

The peptide contained in the vaccine composition of the present invention as the active ingredient (that is, the peptide of the present invention, or the like) is preferably isolated. The "isolation" means an escape from a naturally occurring state by performing an operation to remove factors other than the target component. In the present description, the purity of an "isolated substance X" (the percentage of the weight of the substance X with respect to the total weight of a sample to be evaluated) is usually 70% or more, preferably 80% or more, more preferably 90% or more, further more preferably 99% or more, and yet further more preferably 99.9% or more.

In addition, the vaccine composition of the present invention may further contain an adjuvant that is pharmaceutically acceptable and compatible with the active ingredient. The adjuvant is generally a substance that nonspecifically enhances the immune response of a host, and many various adjuvants are known in this technical field. Examples of the adjuvant include, but are not limited to, the following: complete Freund's adjuvant, incomplete Freund's adjuvant, aluminum hydroxide (for example, Alhydrogel (registered trademark)), aluminum phosphate, aluminum chloride, N-acetyl-muramyl-L-threonyl-D-isoglutamine (thr-MDP), N-acetyl-normuramyl-L-alanyl-D-isoglutamine (nor-MDP), N-acetyl-muramyl-L-alanyl-D-isoglutaminyl-L-alanine-2-(1'-2'-dipalmitoyl-sn-glycero-3-hydroxyphosphoryloxy)-ethylamine (MTP-PE), Quill A (registered trademark), lyso-lecithin, a saponin derivative, a pluronic polyol, montanide ISA-50 (Seppic, Paris, France), Bayol (registered trademark), Markol (registered trademark), a CpG oligodeoxy-nucleotide, a cyclodextrin, and OSK-1.

In addition, the vaccine composition of the present invention may further include, for example, a pharmaceutically acceptable carrier.

Examples of the pharmaceutically acceptable carrier include excipients such as sucrose and starch, binders such as cellulose and methyl cellulose, disintegrants such as starch and carboxymethyl cellulose, lubricants such as magnesium stearate and aerosil, flavors such as citric acid and menthol, preservatives such as sodium benzoate and sodium bisulfite, stabilizers such as citric acid and sodium citrate, suspending agents such as methyl cellulose and polyvinyl pyrrolidone, dispersants such as surfactants, diluents such as water and physiological saline, and base waxes, but are not limited thereto.

The vaccine composition of the present invention can also be used in combination with a known preventive agent or therapeutic agent effective for cancer. Examples of such a known preventive agent or therapeutic agent include tyrosine kinase inhibitors such as imatinib and gefitinib, antibody drugs such as trastuzumab and bevacizumab, mTOR inhibitors such as temsirolimus and everolimus, proteasome inhibitors such as bortezomib, PD-1 checkpoint inhibitors such as Opdivo and Keytruda, MEK kinase inhibitors such as trametinib, pyrimidine antagonists such as fluorouracil and gemcitabine, folate antagonists such as methotrexate and pemetrexed, alkylating agents such as cyclophosphamide and melphalan, anticancer antibiotics such as doxorubicin and pirarubicin, platinum preparations such as cisplatin and carboplatin, microtubule inhibitors such as paclitaxel and docetaxel, topoisomerase inhibitors such as irinotecan and etoposide, and hormone preparations such as tamoxifen and flutamide, but are not limited thereto. Only one type of such known preventive agent or therapeutic agent may be used in combination with the vaccine composition of the present invention, or a plurality of types may be used in combination. In the present description, the phrase "used in combination" means that the vaccine composition of the present invention and the known preventive agent or therapeutic agent for cancer are used in combination, and the use form thereof is not particularly limited. For example, a pharmaceutical composition containing both the vaccine composition of the present invention and the known preventive agent or therapeutic agent for cancer may be prepared and administered, or the vaccine composition of the present invention and the known preventive agent or therapeutic agent for cancer may be separately formulated without mixing, and may be administered simultaneously or with a time lag through the same or different routes of administration.

Note that the "treatment" of a disease in the present description can include not only cure of the disease but also remission of the disease and improvement of the severity of the disease.

Further, the "prevention" of a disease in the present description includes, in addition to prevention of the onset of the disease, delaying of the onset of the disease. In addition, the "prevention" of a disease in the present description can also include prevention of the recurrence of the disease after treatment, or delaying of the recurrence of the disease after treatment.

Further, the term "vaccine composition" in the present description can also be rephrased as "pharmaceutical composition" or "agent".

2. Method for Treating Cancer Expressing VASH2

In another aspect, the present invention provides a method for treating cancer expressing VASH2, including administering either or both of: (1) a peptide including an amino acid sequence represented by SEQ ID NO: 4; and (2) a peptide including an amino acid sequence represented by SEQ ID NO: 4 conjugated with a carrier protein, to a subject. Hereinafter, this is sometimes referred to as "the treatment method of the present invention".

The peptide, the peptide complex in which the peptide and the carrier protein are conjugated, and the like used in the treatment method of the present invention are the same as those described for the vaccine composition of the present invention.

In the subject to which the treatment method of the present invention can be applied, a subject that has cancer expressing VASH2 is included. Further, the subject may or may not receive treatment of cancer other than the treatment method of the present invention before starting the application of the treatment method of the present invention.

In the treatment method of the present invention, the peptide or the like of the present invention to serve as the active ingredient can be orally or parenterally administered to a subject. In the case of oral administration, the peptide serving as the active ingredient can be degraded in the stomach, and therefore, parenteral administration is preferred. Examples of the parenteral administration include subcutaneous injection, intramuscular injection, local injection, and intraperitoneal administration, but are not limited thereto.

In the treatment method of the present invention, a therapeutically effective amount of the peptide or the like of the present invention is administered to a subject. The therapeutically effective amount can vary depending on the subject to be treated, the route of administration, the type of the peptide to be administered, the administration schedule, or the like, however, in general, the peptide serving as the active ingredient is administered at a dose within a range of 1 μg to 1000 μg, preferably within a range of 20 μg to 100 μg per adult usually two to three times over 4 weeks to 12 weeks. When the antibody titer in the subject decreases, one additional administration may be made on each occasion. An appropriate therapeutically effective amount, an appropriate route of administration, or the like can be suitably selected by those skilled in the art.

In one aspect, the treatment method of the present invention can also be carried out in combination with a treatment method for cancer known per se. Examples of the treatment method for cancer that can be combined with the treatment method of the present invention include surgical treatment, drug therapy, and radiation therapy, but are not limited thereto. In particular, it may sometimes be preferred to carry out the treatment method of the present invention in combination with cancer immunotherapy (a dendritic cell vaccine or a cancer vaccine) or gene therapy. Although not wishing to be bound by theory, this is because VASH2 makes tumor blood vessels immature and further increases the drug resistance of cancer cells so that the drug sensitivity of cancer cells is increased by controlling VASH2, and a combined effect thereof with the anticancer agent is expected in conjunction with the improvement of delivery of the anticancer agent by normalization of the blood vessels. In addition, this is because when the tumor blood vessels are normalized by controlling VASH2, the blood flow is improved to eliminate a low oxygen condition, so that the effect of radiation therapy is expected to increase or cancer immunity is expected to be activated.

3. Method for Preventing Cancer Expressing VASH2

In another aspect, the present invention provides a method for preventing cancer expressing VASH2, including administering either or both of: (1) a peptide including an amino acid sequence represented by SEQ ID NO: 4; and (2) a peptide including an amino acid sequence represented by SEQ ID NO: 4 conjugated with a carrier protein, to a subject. Hereinafter, this is sometimes referred to as "the preventive method of the present invention".

The peptide, the complex in which the peptide and the carrier protein are conjugated, and the like used in the preventive method of the present invention are the same as those described for the vaccine composition of the present invention.

In the subject to which the preventive method of the present invention can be applied, a subject that may have cancer expressing VASH2 is included. Such a subject can be identified by, for example, a method known per se such as presymptomatic genetic diagnosis.

In the preventive method of the present invention, the peptide or the like of the present invention can be orally or parenterally administered to a subject. Examples of parenteral administration include subcutaneous injection, intramuscular injection, local injection, and intraperitoneal administration, but are not limited thereto.

In the preventive method of the present invention, a preventively effective amount of the peptide or the like of the present invention is administered to a subject. The preventively effective amount can vary depending on the gender or body weight of the subject, the route of administration, the type of the peptide to be administered, the administration schedule, or the like, however, in general, the peptide serving as the active ingredient is administered at a dose within a range of 1 μg to 1000 μg, preferably within a range of 20 μg to 100 μg per adult usually two to three times over 4 weeks to 12 weeks. When the antibody titer in the subject decreases, one additional administration may be made on each occasion. An appropriate effective amount, an appropriate route of administration, an appropriate administration schedule, or the like can be suitably determined while observing the antibody titer in the subject.

In one aspect, the preventive method of the present invention may also be achieved by producing edible cereal grains that express and accumulate the peptide or the like of the present invention to serve as the active ingredient by a genetic engineering method or seeds thereof (for example, rice, soybeans, wheat, or the like), and ingesting them on a daily basis.

In another aspect of the preventive method of the present invention, the preventive method of the present invention can be a method for preventing the recurrence of cancer expressing VASH2 in a subject that had the cancer before. In other words, a preferred subject to which the preventive method of the present invention is applied can be a subject that had cancer expressing VASH2.

Examples of the "subject that had cancer expressing VASH2" include a subject in which cancer tissue was removed by surgical operation, and a subject in which cancer tissue was eliminated by chemotherapy, radiation therapy, and/or immunotherapy, or the like, but are not limited thereto. Further, among the subjects, a subject having cells highly expressing VASH2 as compared with a normal subject can be a preferred subject to which the preventive method of the present invention is applied. Note that the phrase "highly expressing VASH2" refers to that when the expression level of VASH2 is semiquantified into the following scores: 0: negative, 1: weakly positive, 2: moderately positive, and 3: strongly positive by comparison with the expression level of VASH2 in monocytes in cancer stroma, a score of 1 or more is defined as positive, and particularly preferably, a score of 3 is defined as high expression. Note that examples of the cancer highly expressing VASH2 include ovarian cancer, liver cancer, and pancreatic cancer, but are not limited thereto.

In the present aspect, the peptide or the like of the present invention can be orally or parenterally administered to a subject. Examples of parenteral administration include subcutaneous injection, intramuscular injection, local injection, and intraperitoneal administration, but are not limited thereto.

In the present aspect, a preventively effective amount of the peptide or the like of the present invention is administered to a subject. The preventively effective amount can vary depending on the gender or body weight of the subject, the route of administration, the type of the peptide to be administered, the administration schedule, or the like, however, in general, the peptide serving as the active ingredient is administered at a dose within a range of 1 µg to 1000 µg, preferably within a range of 20 µg to 100 µg per adult usually two to three times over 4 weeks to 12 weeks. When the antibody titer in the subject decreases, one additional administration may be made on each occasion. An appropriate effective amount, an appropriate route of administration, an appropriate administration schedule, or the like can be suitably determined while observing the antibody titer in the subject.

4. Method for Inhibiting Metastasis of Cancer Expressing VASH2

In addition, the present invention provides a method for inhibiting metastasis of cancer expressing VASH2, including administering either or both of:

(1) a peptide including an amino acid sequence represented by SEQ ID NO: 4; and (2) a peptide including an amino acid sequence represented by SEQ ID NO: 4 conjugated with a carrier protein, to a subject. Hereinafter, this is sometimes referred to as "the metastasis inhibition method of the present invention".

The peptide, the peptide complex in which the peptide and the carrier protein are conjugated, and the like used in the metastasis inhibition method of the present invention are the same as those described for the vaccine composition of the present invention.

By applying the metastasis inhibition method of the present invention, the metastasis of cancer can be inhibited as long as it is cancer expressing VASH2. Examples of the cancer expressing VASH2 include pancreatic cancer, ovarian cancer, bile duct cancer, esophageal cancer, stomach cancer, colon cancer, liver cancer, gallbladder cancer, breast cancer, oral cancer, cervical cancer, endometrial cancer, renal cell cancer, bladder cancer, prostate cancer, a testicular tumor, lung cancer, skin cancer, and a brain tumor, but are not limited thereto. The cancer expressing VASH2 can be easily identified by those skilled in the art using a method known per se such as immunostaining or Western blotting. Although not wishing to be bound by theory, in the metastasis inhibition method of the present invention, the inhibition is accompanied by induction of an anti-VASH2 antibody, and therefore, as a more preferred subject to which the method is applied, a subject which has cancer highly expressing VASH2 can be exemplified. Note that the phrase "highly expressing VASH2" refers to that when the expression level of VASH2 is semiquantified into the following scores: 0: negative, 1: weakly positive, 2: moderately positive, and 3: strongly positive by comparison with the expression level of VASH2 in monocytes in cancer stroma, a score of 1 or more is defined as positive, and particularly preferably, a score of 3 is defined as high expression. Note that examples of the cancer highly expressing VASH2 include ovarian cancer, liver cancer, and pancreatic cancer, but are not limited thereto.

In the metastasis inhibition method of the present invention, the peptide serving as the active ingredient can be orally or parenterally administered to a subject. Examples of parenteral administration include subcutaneous injection, intramuscular injection, local injection, and intraperitoneal administration, but are not limited thereto.

In the metastasis inhibition method of the present invention, an amount effective for inhibiting metastasis of the peptide or the like of the present invention is administered to a subject. The effective amount for metastasis inhibition can vary depending on the subject, the route of administration, the type of the peptide to be administered, the administration schedule, or the like, however, in general, the peptide serving as the active ingredient is administered at a dose within a range of 1 µg to 1000 µg, preferably within a range of 20 µg to 100 µg per adult usually two to three times over 4 weeks to 12 weeks. When the antibody titer in the subject decreases, one additional administration may be made on each occasion. An appropriate effective amount, an appropriate route of administration, an appropriate administration schedule, or the like can be suitably determined while observing the antibody titer in the subject.

5. Antibody or Immunologically Active Fragment Thereof

In still another aspect, the present invention provides an antibody against VASH2 or an immunologically active fragment thereof that specifically recognizes an amino acid sequence represented by SEQ ID NO: 4 (hereinafter sometimes referred to as "the antibody or the like of the present invention"). The antibody or the like of the present invention inhibits the function of VASH2 in a subject to which the antibody or the like is administered. Accordingly, the growth and/or migration of cancer cells expressing VASH2 is inhibited. As a result, the antibody or the like of the present invention can treat or prevent cancer expressing VASH2 or inhibit metastasis of the cancer cells. With respect to the production and use of a pharmaceutical composition containing the antibody or the like of the present invention, WO 2014/087810 can be referred to.

The antibody or the like of the present invention is not particularly limited as long as it is an antibody that recognizes an amino acid sequence represented by SEQ ID NO: 4 on the VASH2 protein and inhibits the function of VASH2, and may be any of a polyclonal antibody and a monoclonal antibody, but is preferably a monoclonal antibody. In addition, in consideration of use thereof as a pharmaceutical for treating or preventing cancer expressing VASH2, or inhibiting metastasis of the cancer, the antibody or the like of the present invention is desirably a chimeric antibody, a humanized antibody, or a human antibody, and more preferably a humanized antibody or a human antibody. Such an antibody can be produced by a production method for a polyclonal antibody or a monoclonal antibody known per se using the above-mentioned "peptide or the like of the present invention" as an immunogen.

In the present invention, the "immunologically active fragment" means a partial region of a naturally occurring antibody having a desired activity. Specific examples thereof include a F(ab')$_2$, a Fab', a Fab, an antibody fragment containing an Fc region, an Fv (a variable fragment of an antibody), a single-chain antibody (sFv), a dsFv (a disulphide stabilized Fv), and a dAb (a single-domain antibody), but are not limited thereto. Such an immunologically active fragment can be produced by treating a naturally occurring antibody with a specific peptidase or the like, or using a genetic engineering method.

In a preferred aspect, the antibody and/or the immunologically active fragment thereof of the present invention is isolated. The "isolation" means that an escape from a naturally occurring state by performing an operation to remove factors other than the target component. In the present description, the purity of an "isolated substance X" (the percentage of the weight of the substance X with respect to the total weight of a sample to be evaluated) is usually 70% or more, preferably 80% or more, more preferably 90% or more, further more preferably 99% or more, and yet further more preferably 99.9% or more.

In the present description, the clause that the antibody or the like of the present invention "specifically recognizes" an antigen (that is, a peptide composed of an amino acid sequence represented by SEQ ID NO: 4 or a polypeptide containing the peptide) means that the $K_D$ value for the binding affinity to the antigen of the antibody or the like of the present invention is $1 \times 10^{-7}$ M or less (preferably, $1 \times 10^{-8}$ M or less, more preferably $1 \times 10^{-9}$ M or less, and most preferably, $1 \times 10^{-10}$ M or less).

The present invention will be more specifically described in the following Examples, but the present invention is by no means limited to these examples.

EXAMPLES

Figure 1:
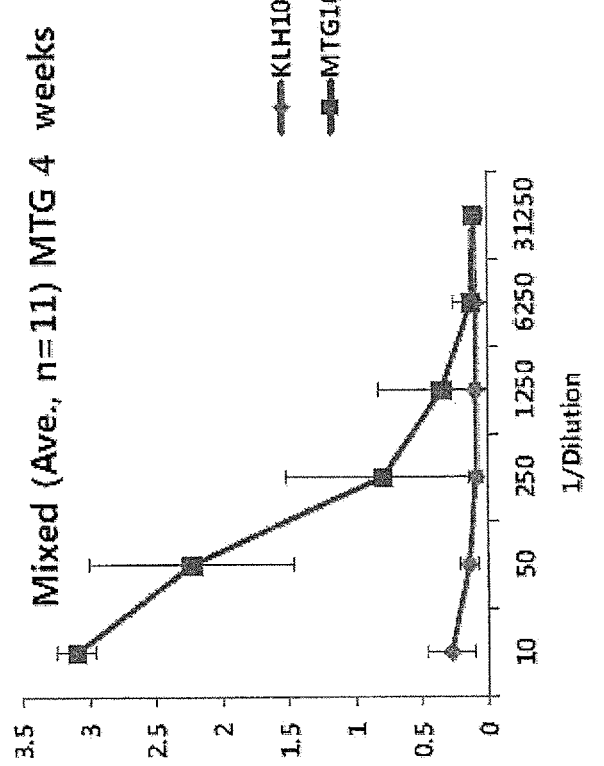
FIG. 1 is a diagram showing homology between human VASH2 (SEQ ID NO: 1) and human VASH1 (SEQ ID NO: 2). Two types of sequences composed of 10 amino acids surrounded by a frame line represent peptide sequences (SEQ ID NOS: 4 and 5) used for inducing production of an antibody that recognizes a VASH2 protein.

[Example 1] Induction of Anti-VASH2 Antibody by Administration of Peptide Vaccine C57BL/6J male mice aged 8 weeks were purchased from Charles River Laboratories Japan, Inc. After the delivery, the mice were reared in an environment where the room temperature and the light and dark cycles were maintained, and were provided with feed and water ad libitum. As a candidate sequence leading to activation of helper T cells by MHC class II, two peptide sequences: MTGSAADTHR (SEQ ID NO: 4; hereinafter, a peptide composed of the amino acid sequence is referred to as "MTG peptide") and RRRQASPPRR (SEQ ID NO: 5; hereinafter, a peptide composed of the amino acid sequence is referred to as "RRR peptide"), each of which is not common to VASH1 in the VASH2 sequence were selected (FIG. 1). With respect to these peptides, peptide vaccines using KLH as a carrier were constructed. Note that for the conjugation of each peptide with KLH, a glutaraldehyde method was used. When the amount of the peptide introduced into KLH was measured for each of the obtained peptide vaccines, the amount of MTG was 66 to 70 nmol/mg of the conjugate, and the amount of RRR was 62 to 76 nmol/mg of the conjugate. Subsequently, 5 µg of KLH (control) and 20 µg of each of the KLH-antigen complexes were prepared with physiological saline so that the total amount was 50 µL, respectively, whereby KLH-mixed solutions were obtained. To each of the KLH-mixed solutions (50 µL), an equal amount of complete Freund's adjuvant was added. The obtained mixture was subcutaneously administered to the mice, whereby initial immunization was carried out. After 2 weeks from the administration, booster immunization was carried out by subcutaneously administering a mixture of each of the KLH-mixed solutions (50 µL) and an equal amount of incomplete Freund's adjuvant to the mice. Further, after 2 weeks from the booster immunization (after a total of 4 weeks), an increase in the antibody titer in the blood of each of the immunized mice was verified by ELISA.

The measurement of the antibody titer by ELISA was carried out as follows. After 2 weeks from the booster immunization (after a total of 4 weeks), the blood was collected from the facial vein of each of the immunized mice, and the serum separated from the blood was subjected to ELISA. By using 50 mM carbonate buffer, peptide-conjugated BSA was prepared at 10 µg/mL, and further a recombinant VASH2 protein was prepared at 1 µg/mL, each of which was added at 50 µL/well, and the resultant was left to stand overnight at 4° C. After the solution in each well was removed, 5% skim milk was added at 150 µL/well. After the resultant was left to stand at room temperature for 2 hours, the solution was removed, and subsequently, a serum sample diluted by 20 to 62500 times with 5% skim milk was added at 50 µL/well, and the resultant was left to stand overnight at 4° C. Subsequently, washing was carried out with PBS (200 µL/well×6 times), and thereafter, a secondary antibody (HRP-conjugated anti-Mouse IgG) diluted by 1000 times with 5% skim milk was added at 50 µL/well. After the resultant was left to stand at room temperature for 3 hours, washing was carried out with PBS (200 µL/well×3 times). Thereafter, tetramethylbenzidine (TMB) was added at 50 µL/well, and the resultant was left to stand at room temperature under light shielding. After 30 minutes, the reaction was stopped by adding 0.5 N H$_2$SO$_4$ at 50 µL/well, and an absorbance (450 nm) was measured using a microplate reader.

The results are shown in FIG. 3. As shown in FIG. 3, in the case of both the MTG peptide vaccine and the RRR peptide vaccine, a significant increase in the antibody titer against the antigen peptide was observed (FIGS. 3(a) and 3(c)). On the other hand, against the recombinant human VASH2 protein, only in the case of the MTG peptide vaccine, a significant increase in the antibody titer was confirmed, and in the case of the RRR peptide vaccine, a significant increase in the antibody titer was not confirmed (FIGS. 3(b) and 3(d)). From the results, it is considered that the RRR peptide vaccine can induce the production of an antibody that can bind to the antigen peptide itself, but the antibody cannot bind to the VASH2 protein. On the other hand, it is considered that the antibody whose production is induced by the MTG peptide vaccine can bind not only to the antigen peptide itself, but also to the VASH2 protein, and therefore, in the following Examples, various verifications were carried out using the MTG peptide vaccine.

[Example 2] Verification of Tumor Growth Inhibitory Effect (1)

After 2 weeks from the administration of each peptide vaccine and incomplete Freund's adjuvant in Example 1 (on day 29 after the initial peptide vaccine administration), mouse-derived tumor cells were implanted in an immunized mouse, whereby a subcutaneous implant model was prepared. Specifically, mouse lung cancer cells (Lewis lung cancer cells (LLC)) or mouse melanoma cells (B16F1) (all have C57BL/6J as a genetic background) cultured in a RPMI+10% FBS medium were collected by centrifugation, and a cell suspension ($1.0 \times 10^8$ cells/mL) was prepared with a serum-free medium, and 0.1 mL ($1.0 \times 10^7$ cells/animal) of the cell suspension was implanted in a right axillary subcutaneous region of a mouse using a 27G injection needle and a syringe, whereby a subcutaneous implant model of tumor cells was prepared. The tumor growth inhibitory effect of each peptide vaccine was verified by measuring the tumor size at 14 days after the implantation of the tumor cells.

Figure 4:
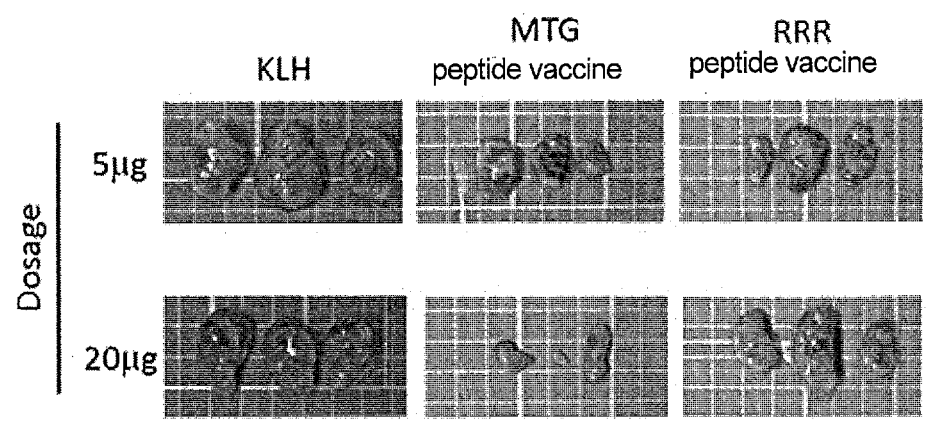
FIG. 4 is a view showing inhibition of tumorigenesis by administration of MTG peptide vaccine or RRR peptide vaccine. Mice injected with peptide vaccine were subcutaneously implanted with Lewis lung cancer cells or B16F1 melanoma cells at 29 days after the injection of the vaccine. At 14 days after the implantation, the size of a tumor formed was measured. In a group to which the MTG peptide vaccine was administered, marked inhibition of tumor growth was observed in both Lewis lung cancer cells or B16F1 melanoma cells.
Figure 4:
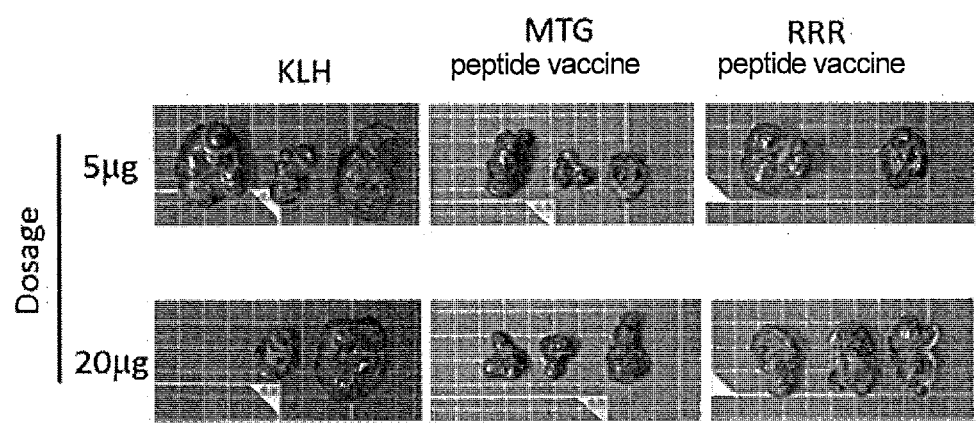

The results are shown in FIG. 4. As shown in FIG. 4, marked inhibition of tumorigenesis was observed in mice immunized with the MTG peptide vaccine against any tumor cells. On the other hand, the RRR peptide vaccine could not inhibit tumorigenesis in the subcutaneous implant model, and it was indicated that the inhibition of the function of VASH2 by an antibody induced by the MTG peptide vaccine results in an antitumor effect.

[Example 3] Verification of Effect on Migration Ability of Cancer Cells

The mouse implanted with the tumor cells in Example 2 was sacrificed two weeks after implantation of the tumor cells, and a tumor was excised from the right axillary subcutaneous region. By using RNeasy Plus Kit (Qiagen, Inc.), extraction of the total RNA from the excised tumor and purification thereof were carried out. By using the obtained total RNA as a template, cDNA was synthesized by reverse transcription reaction. The cDNA was analyzed by performing real-time PCR using a mixed solution of the obtained cDNA and SYBR green (TAKARA BIO, Inc.). Note that the primers used in the real-time PCR are as shown in the following Table 1.

TABLE 1

| Primer name | Forward | Reverse |
|---|---|---|
| mCD31 | 5'-TTCAGCGAGAT CCTGAGGGTC-3' (SEQ ID NO: 6) | 5'-CGCTTGGGTGT CATTCACGAC-3' (SEQ ID NO: 7) |
| mTwist1 | 5'-GCCAGGTACA TCGACTTCCT-3' (SEQ ID NO: 8) | 5'-CCAGACGGAG AAGGCGTAG-3' (SEQ ID NO: 9) |
| mSnail | 5'-GAGGACAGTG GCAAAAGCTC-3' (SEQ ID NO: 10) | 5'-CAGCTGCTTG GGAAGTTGG-3' (SEQ ID NO: 11) |
| mZeb1 | 5'-CTCCCAGTCA GCCACCTTTA-3' (SEQ ID NO: 12) | 5'-GGTTCACAGA ATCGGCGATC-3' (SEQ ID NO: 13) |

Figure 5:
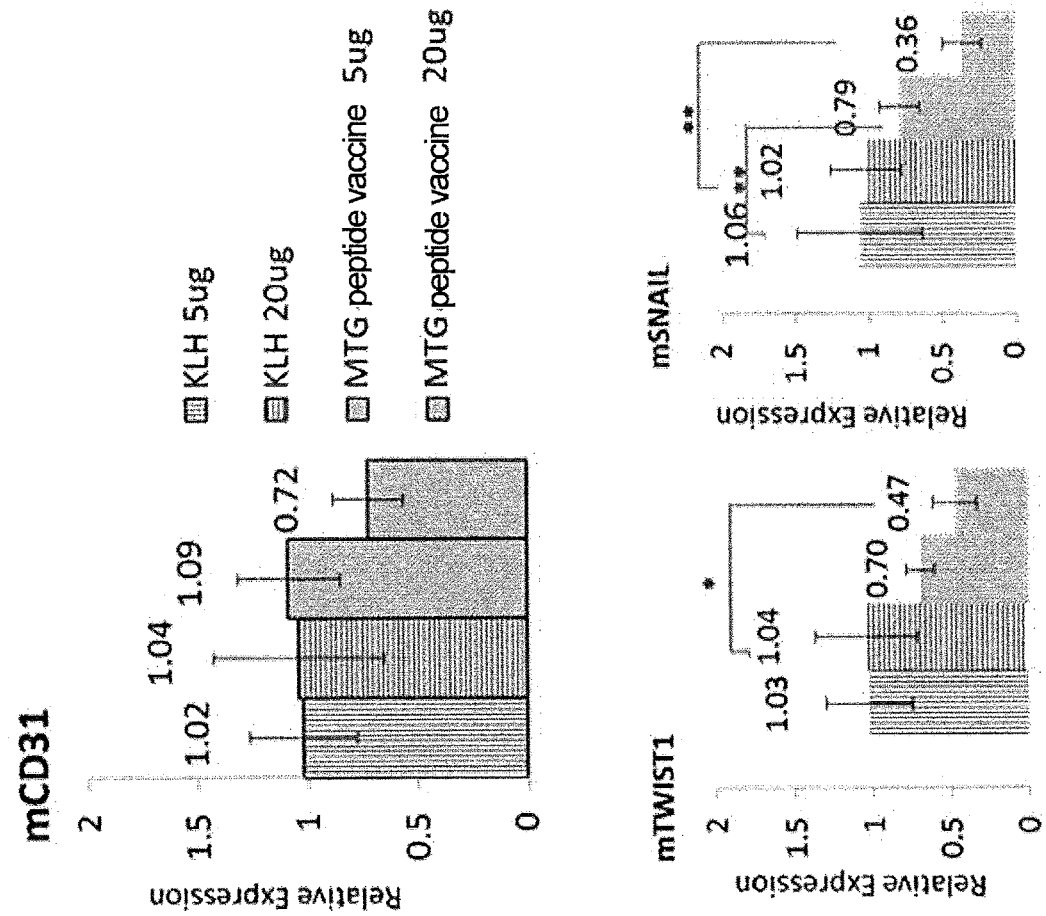
FIG. 5 is a view showing changes in gene expression in tumor tissue by administration of MTG peptide vaccine. In the case of mCD31 that is an angiogenesis marker, no significant difference was observed, however, in the case of administration of the MTG peptide vaccine at a high dose (20 μg), a tendency to inhibit the expression was observed. Further, the expression of each of mTwist1, mSnail, and mZeb1 that are epithelial-mesenchymal transition markers was significantly inhibited depending on the dose of the MTG peptide vaccine.

The results are shown in FIG. 5. Although no statistically significant difference was observed with respect to mCD31 that is an angiogenesis marker, the expression of mCD31 was inhibited in the mouse to which 20 μg of the MTG peptide vaccine was administered. In addition, with respect to mTwist1, mSnail1 and mZeb1 that are epithelial-mesenchymal transition markers, a dose-dependent expression inhibitory effect of the MTG peptide vaccine was observed.

[Example 4] Verification of Migration Inhibitory Effect of Various Cancer Cells

By using the serum derived from a mouse in which an increase in the antibody titer against the recombinant human VASH2 protein by administration of the MTG peptide vaccine was confirmed, the effect on the migration ability of various types of cancer cells was examined by an in vitro wound migration method. Mouse-derived Lewis lung cancer cells and human-derived RH30 rhabdomyosarcoma cells were added to a 6-well plate at $1.0 \times 10^6$ cells each. After 24 hours, a formed cell monolayer was wounded and linearly exfoliated. After the exfoliation, the medium was replaced with fresh 0.5% FBS+RPMI medium supplemented with 1% mouse serum. At 24 hours and 48 hours after the medium replacement, the image of the cell monolayer was captured using an IX71 inverted microscope (manufactured by Olympus Corporation), and a cell migration distance of each time zone was analyzed using ImageJ software. The analysis was carried out according to the following formula.

Cell migration distance (%)=$\{(A-B)/A\} \times 100$

A: Width of initial wound, B: Width of wound after 24 hours or 48 hours

Figure 6:
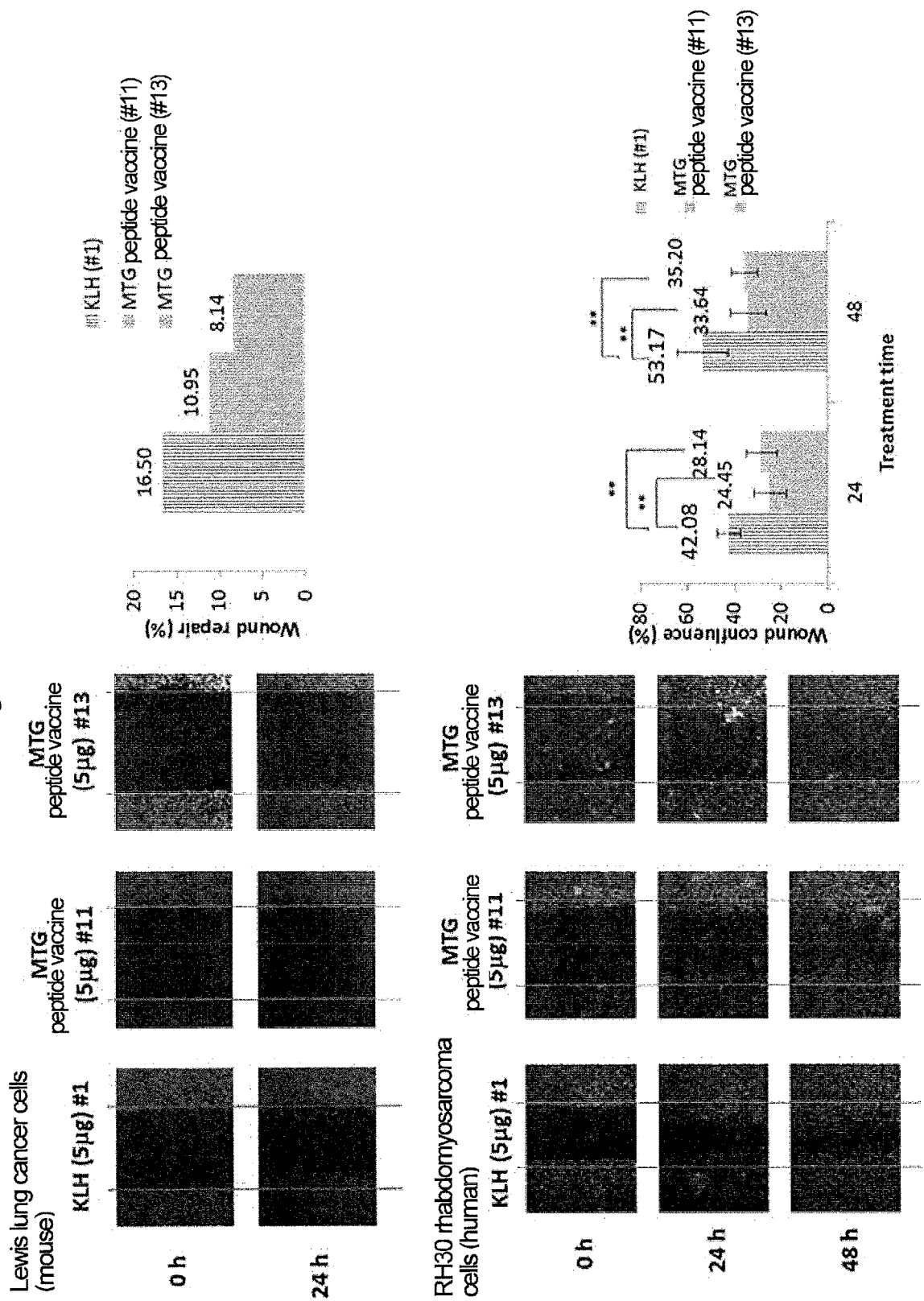
FIG. 6 is a view showing results of examining the effect of serum derived from a mouse whose antibody titer against a recombinant human VASH2 protein has increased by administration of MTG peptide vaccine on the migration ability of cancer cells derived from a human and a mouse using an in vitro wound migration method. It was confirmed that the MTG peptide vaccine has an inhibitory effect not only on the migration of mouse-derived Lewis lung cancer cells, but also on the migration of human-derived RH30 rhabdomyosarcoma cells.

The results are shown in FIG. 6. As shown in FIG. 6, the serum derived from the mouse in which an increase in the antibody titer against the recombinant human VASH2 protein by administration of the MTG peptide vaccine was confirmed exhibited a migration inhibitory effect not only on the mouse-derived Lewis lung cancer cells but also on the human-derived RH30 rhabdomyosarcoma cells. The results indicate that it is possible to produce an antibody that inhibits both mouse VASH2 and human VASH2 using a peptide sequence common to mouse and human.

[Example 5] Verification of Metastasis Inhibitory Effect on Cancer Cells (LLC) In Vivo (1)

Figure 7:
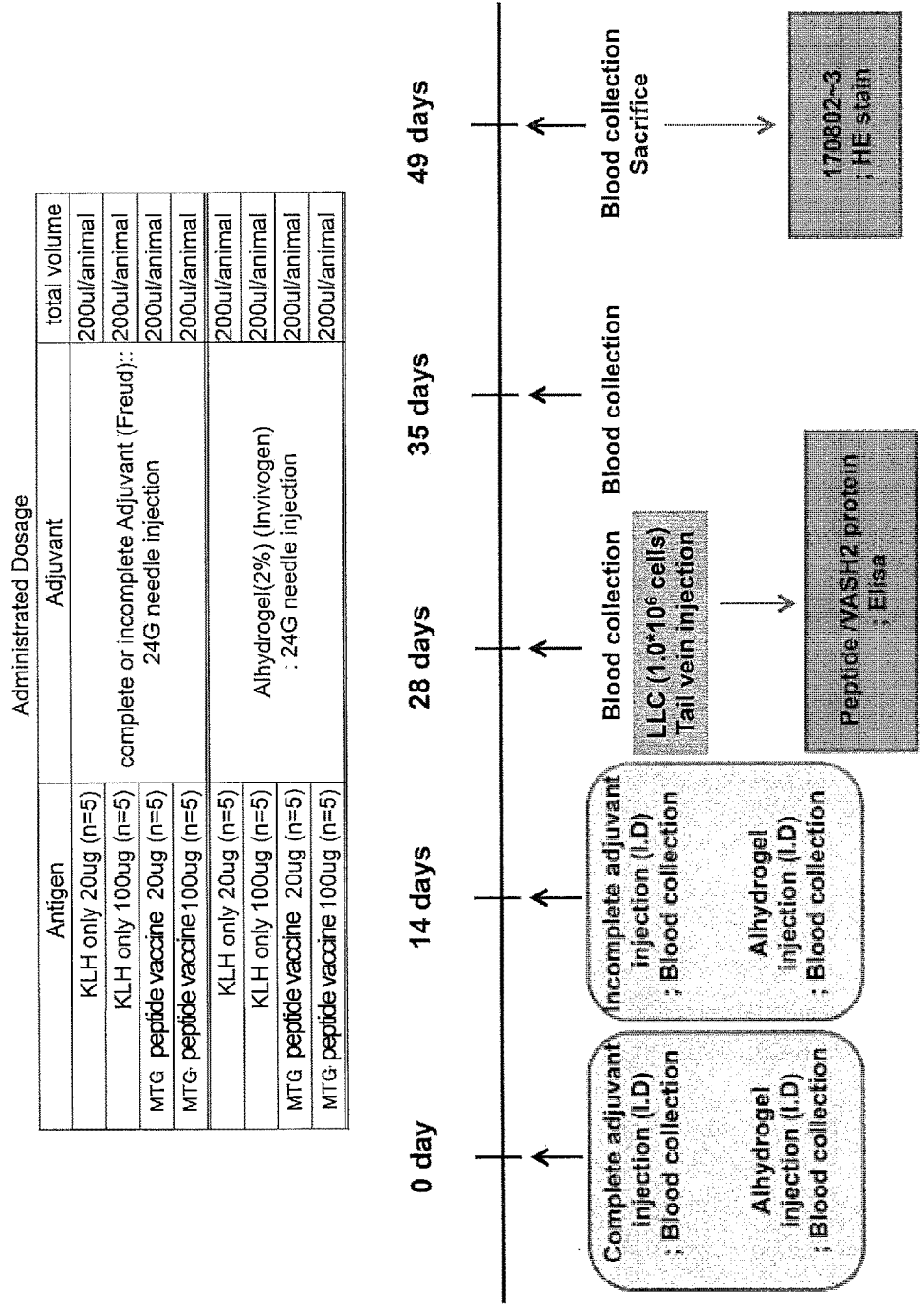
FIG. 7 is a view showing an experimental schedule for verifying the metastasis inhibitory effect of MTG peptide vaccine on cancer cells in vivo.

20 μg or 100 μg of KLH (control) and 20 μg or 100 μg of the peptide represented by SEQ ID NO: 4 conjugated with KLH (MTG peptide vaccine) were prepared with physiological saline so that the total amount was 100 μL, respectively, whereby KLH-mixed solutions were obtained. To each of the KLH-mixed solutions (100 μL), an equal amount of complete Freund's adjuvant or Alhydrogel (registered trademark) (Invitrogen) was added. The obtained mixture (200 μL) was intradermally (ID) administered to C57BL/6J male mice (n=5) aged 8 weeks, whereby initial immunization was carried out (0 day). Incidentally, in the intradermal administration, 200 μL was administered at a dose of 100 μL each to two sites. After 2 weeks from the administration (14 days), booster immunization was carried out by subcutaneously administering a mixture of each of the KLH-mixed solutions (100 μL) and an equal amount of incomplete Freund's adjuvant or Alhydrogel (registered trademark) to the mice. Further, after 2 weeks from the booster immunization (28 days), 0.1 mL ($1.0 \times 10^6$ cells/animal) of a cell suspension of mouse lung cancer cells (LLC) was injected into the immunized mice through the tail vein using a 27 G injection needle and a syringe. Further, at that time point, the blood was collected from each mouse, and the antibody titer of an antibody specific to the VASH2 protein was measured by ELISA. The mice were sacrificed on day 21 after the injection of LLC (49 days), and the lung metastatic lesion was analyzed (FIG. 7).

Specifically, the analysis of the lung metastatic lesion was carried out as follows. The lung was excised from each of the sacrificed mice, and the excised sample was fixed, followed by a dehydration treatment, whereby a paraffin block was prepared. The block was sliced to a thickness of 5 µm, and the resulting section was attached to a microscope slide subjected to a peeling prevention treatment. Subsequently, deparaffinization was carried out, and after washing with running water, the section was immersed in a hematoxylin solution for 3 minutes, and then washed with milliQ water. Subsequently, the section was immersed in a 1% eosin solution for 2 minutes, and then dehydrated using an alcohol, and further cleared with xylene, followed by enclosure, and observation was carried out. Note that the mouse #8 in which Freund's adjuvant was used as the adjuvant and 100 µg of KLH was administered, the mice #7 and #10 in which Alhydrogel (registered trademark) was used as the adjuvant and 100 µg of KLH was administered, and the mouse #17 in which Alhydrogel (registered trademark) was used as the adjuvant and 100 µg of the MTG peptide vaccine was administered died before day 21 after injection of LLC (49 days), and therefore, the lung could not be excised.

Figure 8:
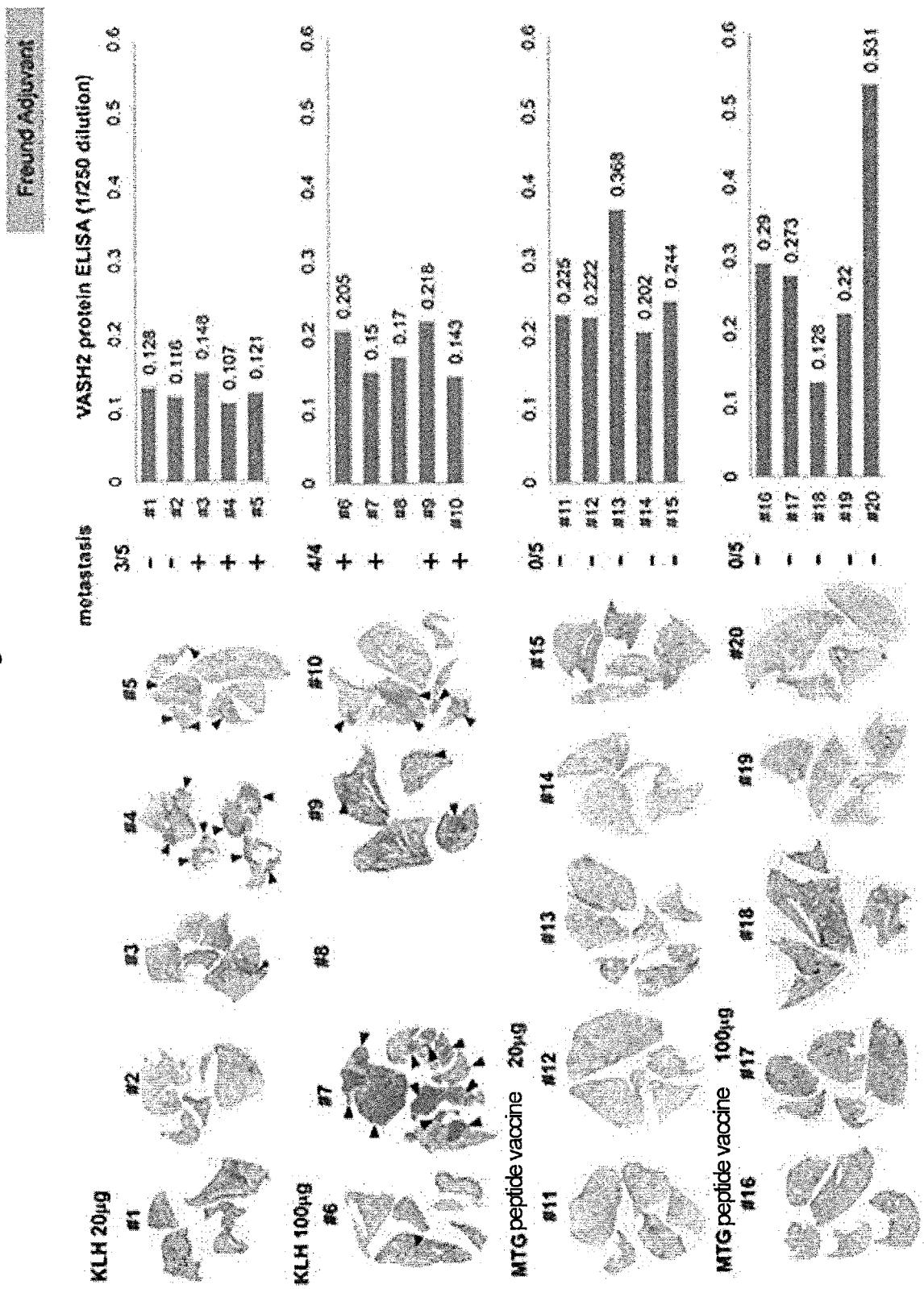
FIG. 8 is a view showing the metastasis inhibitory effect of MTG peptide vaccine when Freund's adjuvant was used as an adjuvant.
Figure 9:
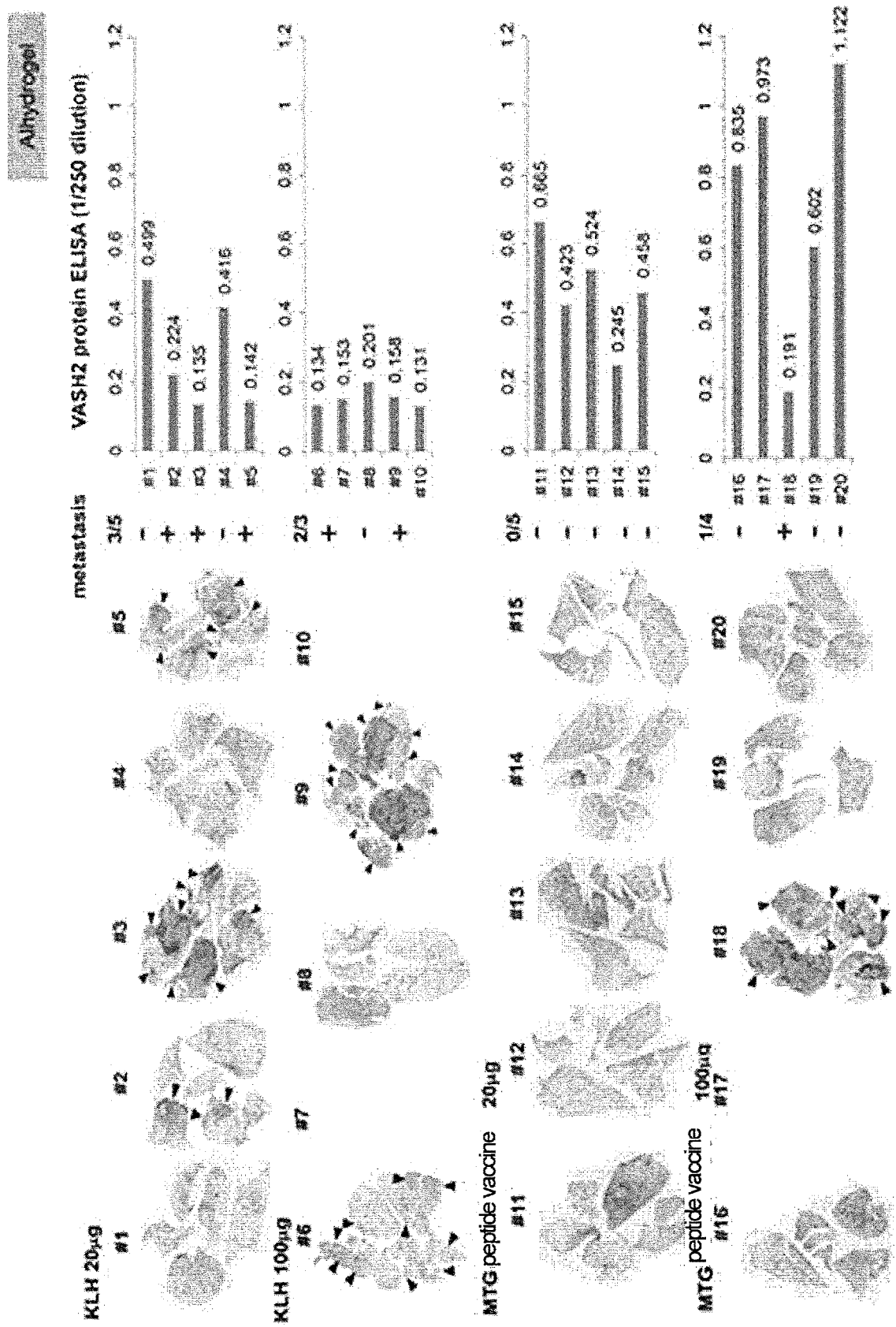
FIG. 9 is a view showing the metastasis inhibitory effect of MTG peptide vaccine when Alhydrogel (registered trademark) was used as an adjuvant.

The results are shown in FIG. 8 (in the case of using Freund's adjuvant) and FIG. 9 (in the case of using Alhydrogel). As shown in each figure, even when either Freund's adjuvant or Alhydrogel was used as the adjuvant, the MTG peptide vaccine promoted the production of an antibody specific to VASH2 and inhibited metastasis of cancer cells.

[Example 6] Verification of Metastasis Inhibitory Effect on Cancer Cells (K5) In Vivo (2)

Figure 10:
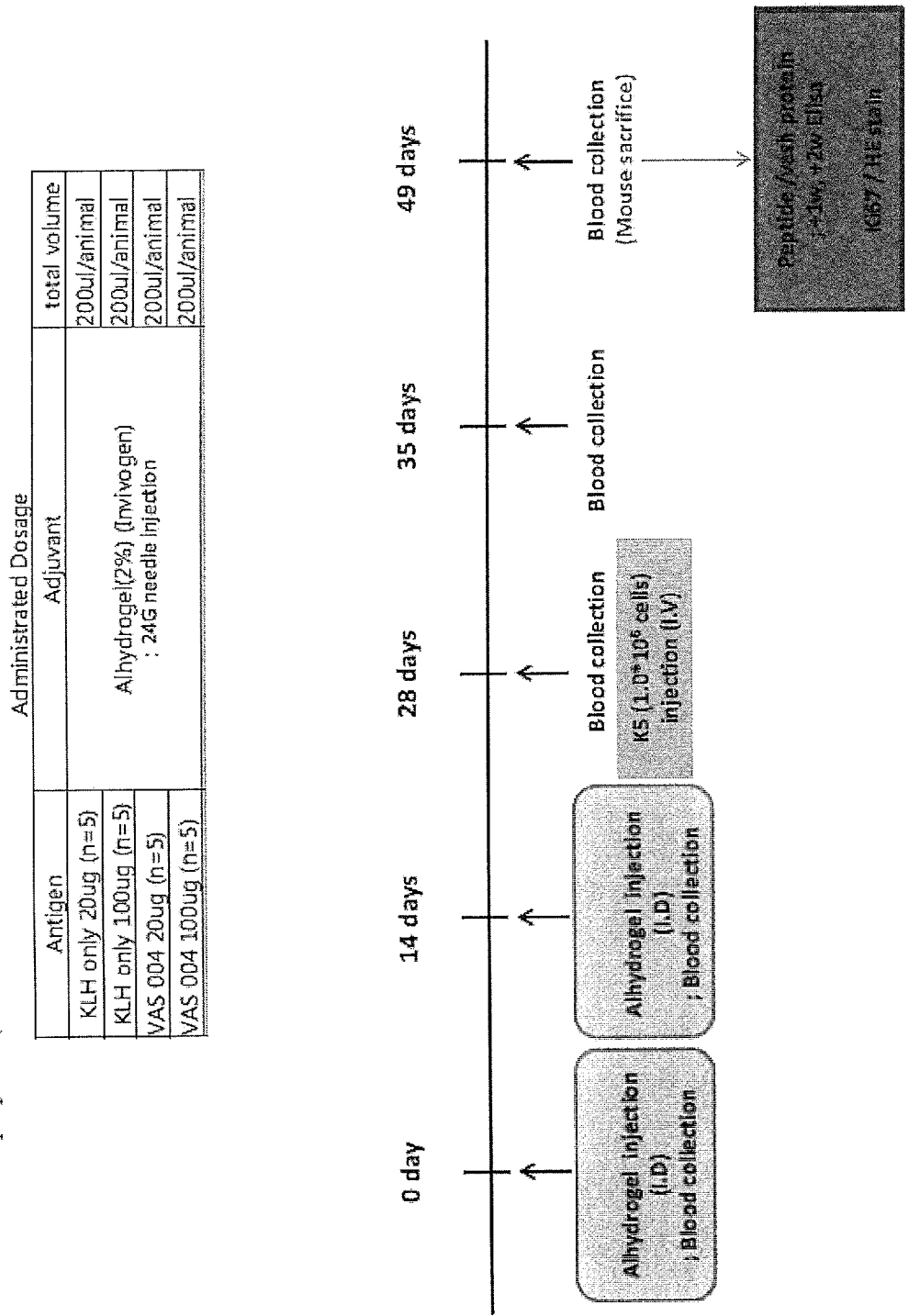
FIG. 10 is a view showing an experimental schedule for verifying the metastasis inhibitory effect of administration of MTG peptide vaccine on cancer cells in vivo.

20 µg or 100 µg of KLH (control) and 20 µg or 100 µg of the MTG peptide vaccine were prepared with physiological saline so that the total amount was 100 µL, respectively, whereby KLH-mixed solutions were obtained. To each of the KLH-mixed solutions (100 µL), an equal amount of Alhydrogel (registered trademark) was added. The obtained mixture (200 µL) was intradermally (ID) administered to C57BL/6J male mice (n=5) aged 8 weeks, whereby initial immunization was carried out (0 day). Incidentally, in the intradermal administration, 200 µL was administered at a dose of 100 µL each to two sites. After 2 weeks from the administration (14 days), booster immunization was carried out by subcutaneously administering a mixture of each of the KLH-mixed solutions (100 µL) and an equal amount of Alhydrogel (registered trademark) to the mice. Further, after 2 weeks from the booster immunization (28 days), 0.1 mL ($1.0 \times 10^6$ cells/animal) of a cell suspension of a pancreatic cancer cell line (K5) established by a conventional method from a KPC mouse (Hamada S, et al. Nrf2 promotes mutant K-ras/p53-driven pancreatic carcinogenesis. Carcinogenesis 38: 661-670, 2017) that is a model mouse following a similar course to human pancreatic cancer was injected into the immunized mice through the tail vein using a 27 G injection needle and a syringe. Further, at that time point, the blood was collected from each mouse, and the antibody titer of an antibody specific to the antigen peptide or the recombinant human VASH2 protein was measured by ELISA. The mice were sacrificed on day 21 after the injection of K5 (49 days), and the lung metastatic lesion was analyzed (FIG. 10). The analysis of the lung metastatic lesion was carried out in the same manner as performed in Example 5.

Figure 11:
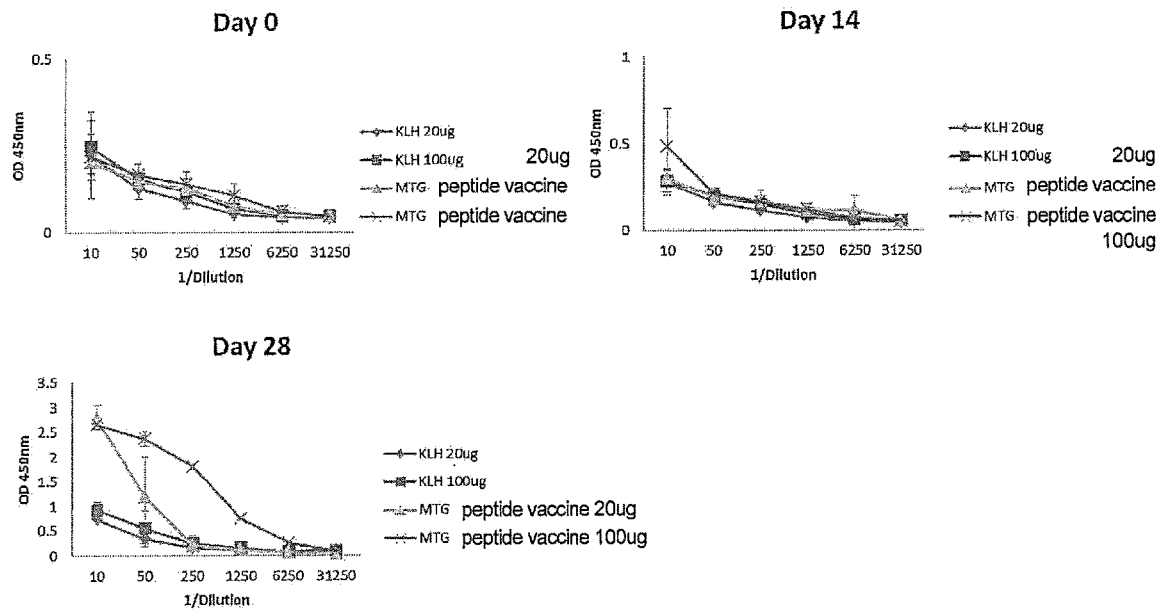
FIG. 11 is a view showing results of verifying an increase in the antibody titer in the blood of mice immunized with MTG peptide vaccine using ELISA.
Figure 11:
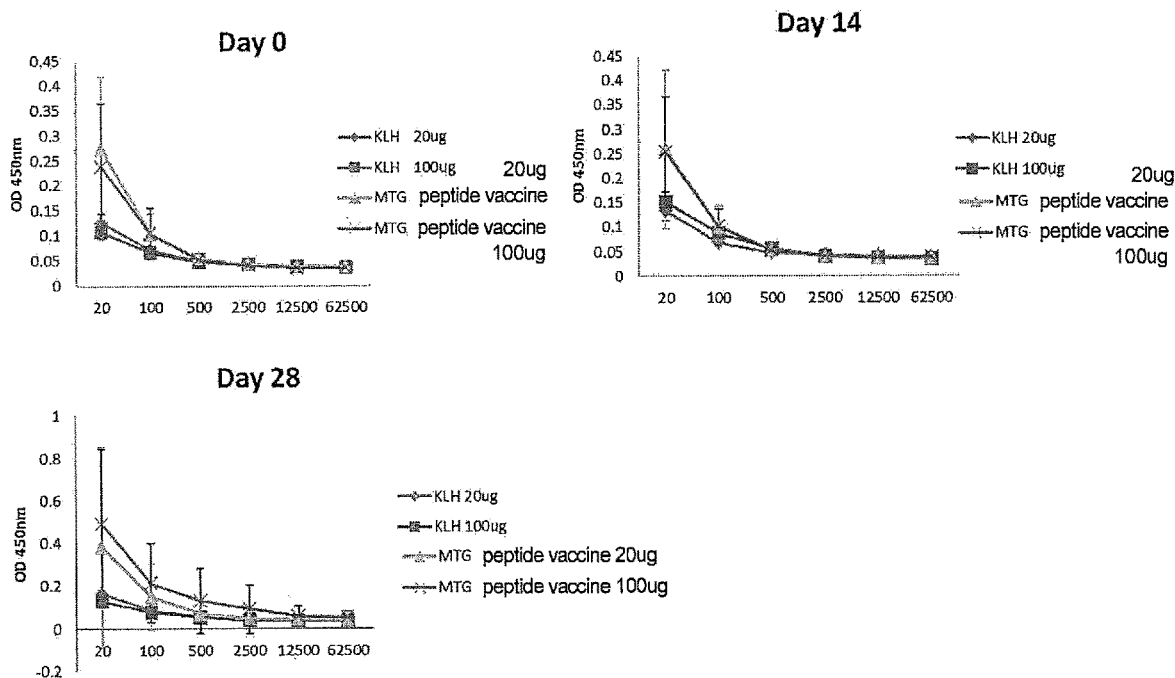
Figure 12:
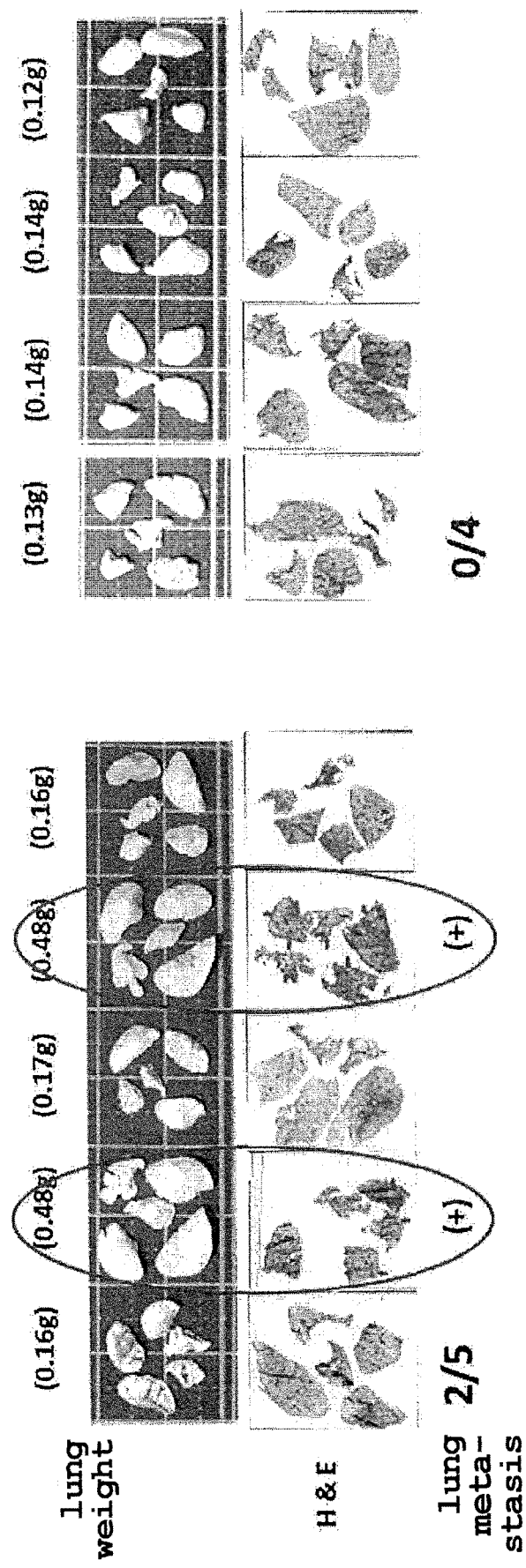
FIG. 12 is a view showing the metastasis inhibitory effect of MTG peptide vaccine.

The results of the antibody titer are shown in FIG. 11, and the results associated with lung metastasis (when immunization was carried out with 100 µg of KLH or the MTG peptide vaccine) are shown in FIG. 12. As shown in FIG. 11, it was indicated that the MTG peptide vaccine promotes the production of an antibody specific to the antigen peptide and the VASH2 recombinant protein. Further, as shown in FIG. 12, lung metastasis was confirmed in 2 out of 5 mice to which only KLH was administered, whereas in the case of the mice immunized with the MTG peptide vaccine, lung metastasis of the pancreatic cancer cells K5 was not confirmed in all four individuals that could be analyzed, and the metastasis inhibitory effect of the MTG peptide vaccine was demonstrated.

Figure 13:
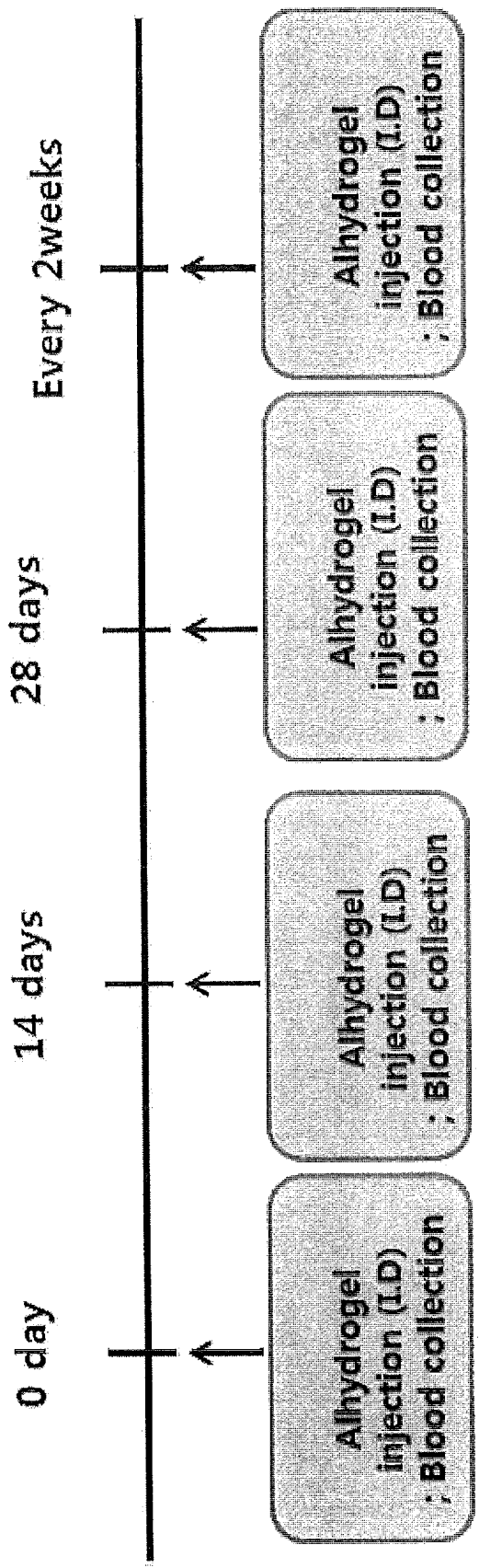
FIG. 13 is a view showing an experimental schedule for verifying the life-extending effect of administration of MTG peptide vaccine to KPC mice.

[Example 7] Verification of Life-Extending Effect of MTG Peptide Vaccine Using KPC Mouse To a KPC mouse (aged 8 weeks at the initial immunization) that is a spontaneous pancreatic cancer model, 100 µg of the MTG peptide vaccine was administered together with Alhydrogel (registered trademark) every two weeks, and the survival rate thereof was confirmed (n=8). A KPC mouse to which 100 µg of KLH was administered according to the same schedule was used as a control (n=7) (FIG. 13).

Figure 14:
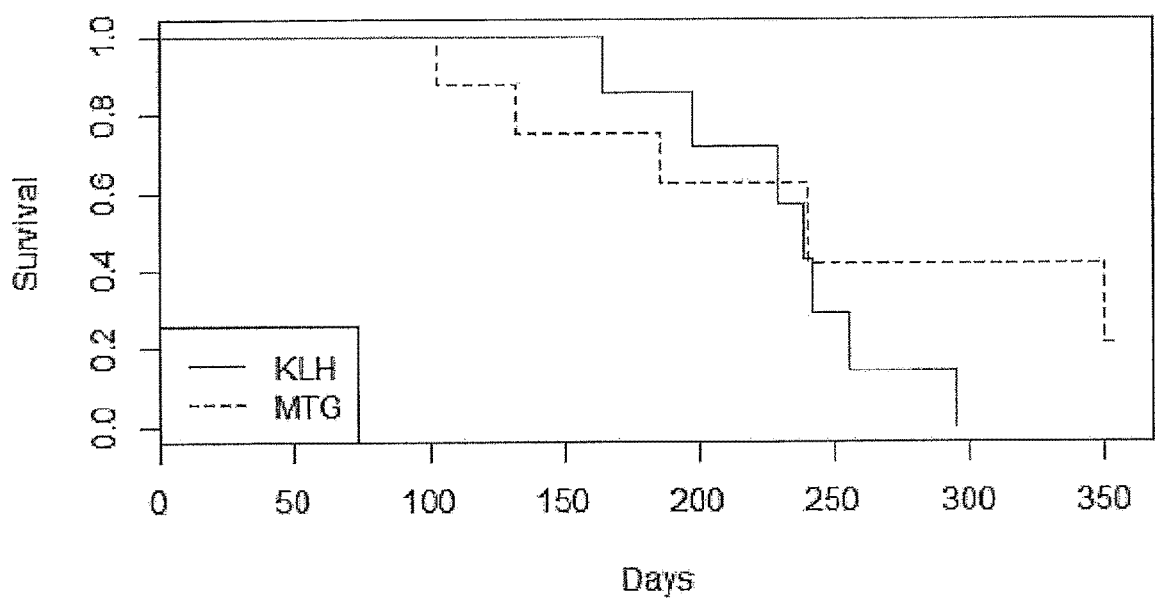
FIG. 14 is a view showing the life-extending effect of administration of MTG peptide vaccine on KPC mice.

The results are shown in FIG. 14. As shown in FIG. 14, in the control group to which KLH was administered, all (n=7) mice died before reaching 300 days after birth. On the other hand, in the mice to which the MTG peptide vaccine was administered, at least 2 mice survived over 300 days after birth (among the mice to which the MTG peptide vaccine was administered, #137, #246, and #256 all survived as of Jul. 29, 2018, and therefore, the numerical value of "Day" in the table is expected to increase further).

[Example 8] Verification of Tumor Growth Inhibitory Effect on Cancer Cells (K5) In Vivo (2)

In Example 6, the metastasis inhibitory effect was tested using C57BL/6J mice allogeneic to K5 cells as recipients, however, for the purpose of eliminating the effect of implantation of allogeneic cancer cells, C57BL/6Jx129SVJ mice with the same genetic background as KPC mice were used as the recipients, and the tumor growth inhibitory effect of the MTG peptide vaccine in a subcutaneous implant model of K5 cells was tested.

Figure 15:
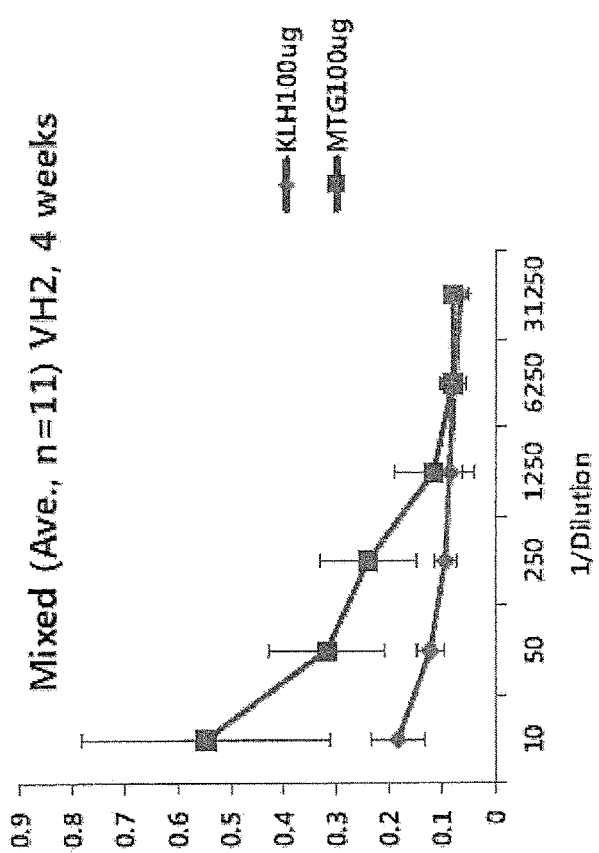
FIG. 15 is a view showing an experimental schedule for verifying the tumor growth inhibitory effect of administration of MTG peptide vaccine on cancer cells in vivo.
Figure 15:
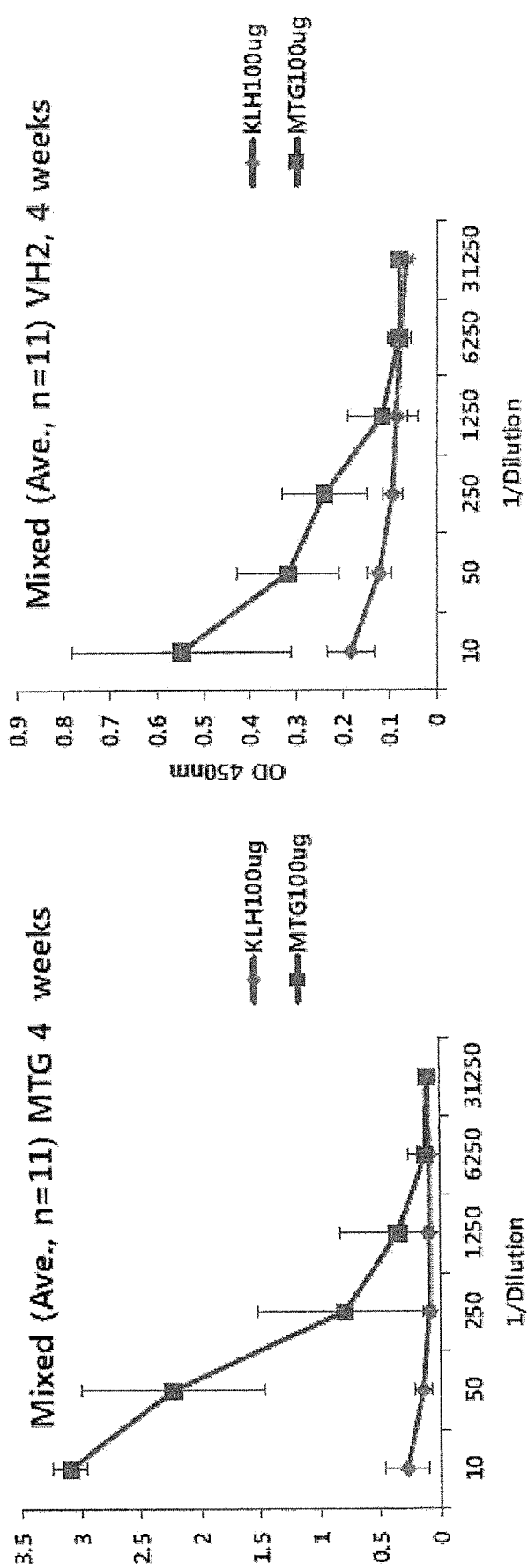

100 µg of KLH (control) or 100 µg of the MTG peptide vaccine was prepared with physiological saline so that the total amount was 100 &L, respectively, whereby KLH-mixed solutions were obtained. To each of the KLH-mixed solutions (100 µL), an equal amount of Alhydrogel (registered trademark) was added. The obtained mixture (200 µL) was intradermally (ID) administered to C57BL/6Jx129SVJ mice aged 8 weeks, whereby initial immunization was carried out (0 day). After 2 weeks from the administration (14 days), booster immunization was carried out. Further, after 2 weeks from the booster immunization (28 days), K5 cells were implanted in each of the mice, whereby a subcutaneous implant model was prepared. In order to confirm that an anti-VASH2 antibody was induced in the mice, the blood was collected at 0 day, 14 day, and 28 day, and the antibody titer was confirmed by ELISA (FIG. 15). Further, by measuring the tumor size at 14, 21, 28, 35, and 40 days after the implantation of the tumor cells (K5), the growth inhibitory effect of the MTG peptide vaccine was verified (Experiment 1; n=2). In addition, the number of individuals was increased, and the tumor size was measured at each day from days 7 to 15 after the implantation of the tumor cells (K5), and it was verified whether or not the MTG peptide vaccine statistically significantly inhibits the tumor growth (Experiment 2; n=11).

Figure 16:
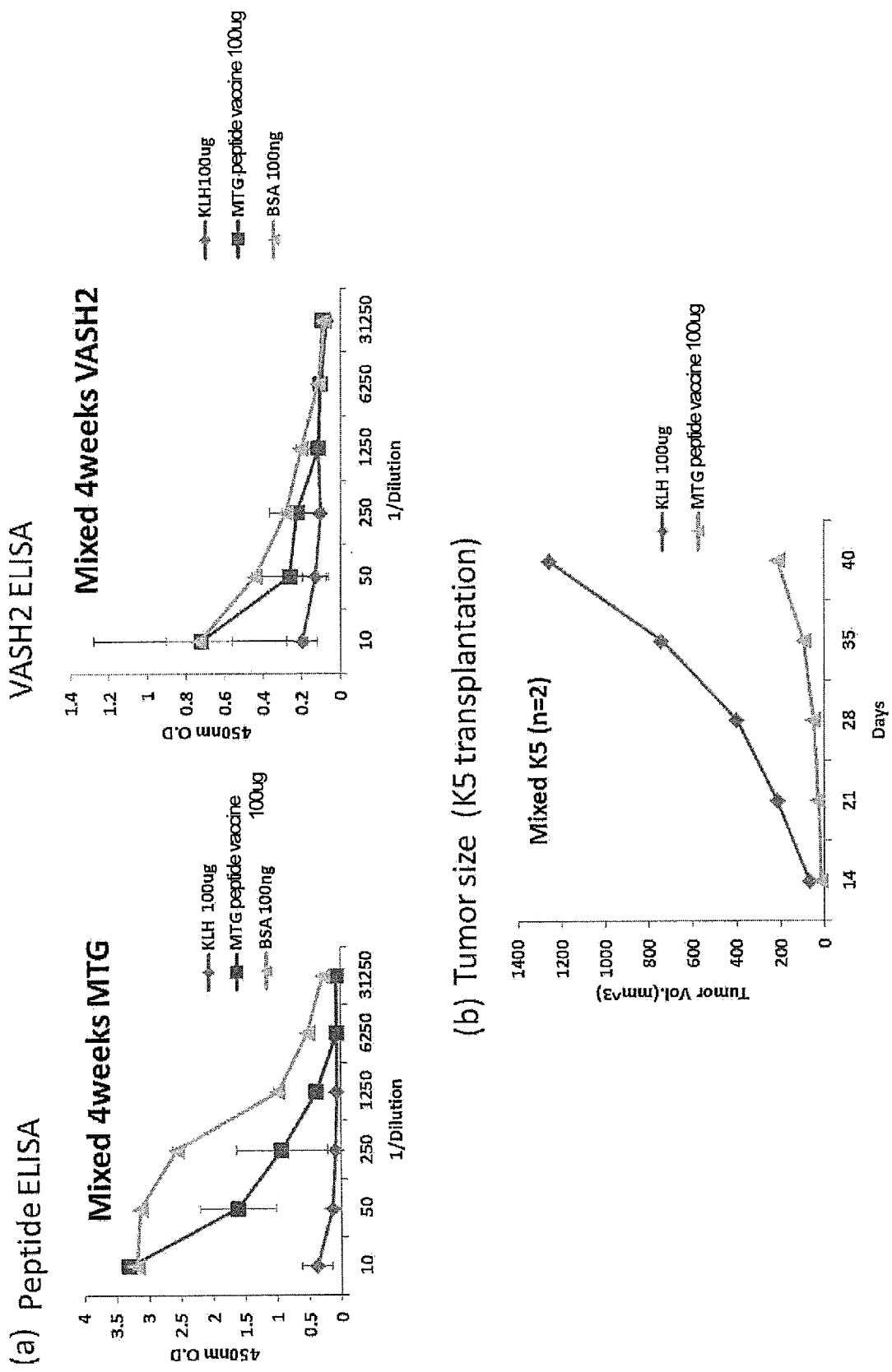
FIG. 16 is a view showing antibody titers at 28 days after administration of vaccine (day 28) (FIG. 16(a)) and tumor sizes at 14 to 40 days after implantation of K5 cells (FIG. 16(b)) in C57BL/6Jx129SVJ mice (n=2) to which MTG peptide vaccine was administered.
Figure 17:
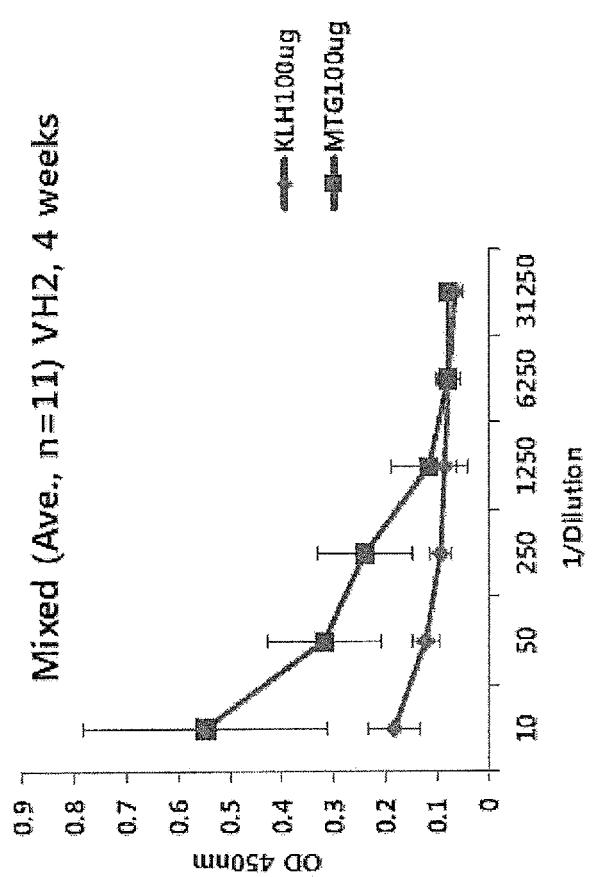
Figures 2, 17:
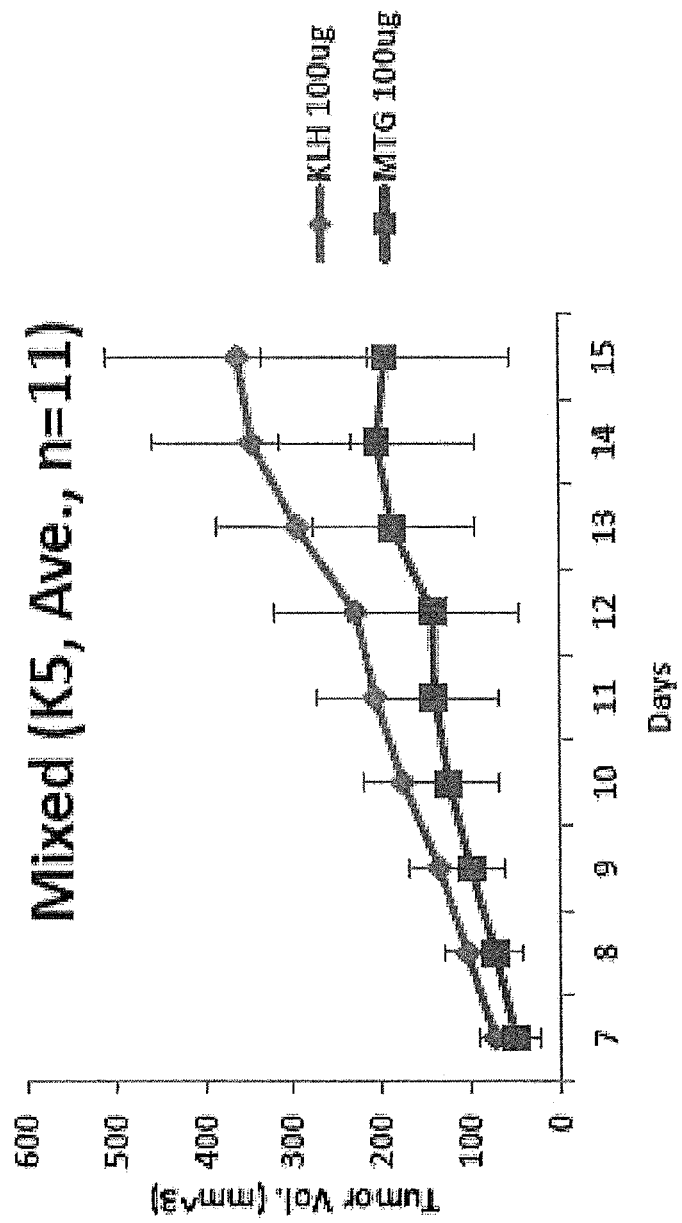

The results of Experiment 1 are shown in FIG. 16, and the results of Experiment 2 are shown in FIGS. 17-1 and 17-2. As shown in FIG. 16(a) and FIG. 17-1, the MTG peptide vaccine induced an antibody that binds to both the antigen peptide (MTG) and the VASH2 recombinant protein. Further, as shown in FIG. 16(b), in the mice immunized with the MTG peptide vaccine, significant inhibition of tumorigenesis was observed. Also in the confirmation experiment (Experiment 2) in which the number of individuals was increased, on day 15 after the implantation, in the mice immunized with the MTG peptide vaccine, tumorigenesis was significantly inhibited as compared with the mice to which KLH was administered (p=0.0002).

INDUSTRIAL APPLICABILITY

According to the present invention, cancer expressing VASH2 can be treated or prevented. Further, according to the present invention, metastasis of cancer expressing VASH2 can be inhibited. Since the peptide vaccine of the present invention can be produced by chemical synthesis and can induce the production of an anti-VASH2 neutralizing antibody via the patient's own immune mechanism, the peptide vaccine is extremely advantageous in that it is inexpensive as compared with an antibody drug and can provide a therapeutic or preventive agent for cancer that exhibits the same effects as an antibody drug.

This application is based on Patent Application No. 2017-166860 filed in Japan (filing date: Aug. 31, 2017), the contents of which are incorporated herein in their entirety.

The invention claimed is:

1. A peptide consisting of the amino acid sequence of SEQ ID NO: 4, wherein the peptide is amidated at the C-terminus.

2. A vaccine composition for treating cancer expressing vasohibin-2 (VASH2), comprising:
   (a) either or both of:
      (1) a peptide consisting of the amino acid sequence of SEQ ID NO: 4, wherein the peptide is amidated at the C-terminus; and
      (2) a peptide consisting of the amino acid sequence of SEQ ID NO: 4 conjugated with a carrier protein, and
   (b) a pharmaceutically acceptable carrier.

3. The vaccine composition according to claim 2, wherein the peptide is amidated at the C-terminus.

4. The vaccine composition according to claim 2, wherein the carrier protein is selected from the group consisting of bovine serum albumin (BSA), rabbit serum albumin (RSA), ovalbumin (OVA), keyhole limpet hemocyanin (KLH), OSK-1, thyroglobulin (TG), and an immunoglobulin.

5. A method for treating cancer expressing VASH2, comprising administering either or both of:
   (1) a peptide including the amino acid sequence of SEQ ID NO: 4; and
   (2) a peptide including the amino acid sequence of SEQ ID NO: 4 conjugated with a carrier protein; to a subject.

6. The method according to claim 5, wherein the peptide is amidated at the C-terminus.

7. The method according to claim 5, wherein the carrier protein is selected from the group consisting of bovine serum albumin (BSA), rabbit serum albumin (RSA), ovalbumin (OVA), keyhole limpet hemocyanin (KLH), OSK-1, thyroglobulin (TG), and an immunoglobulin.

8. The method according to claim 5, wherein the cancer expressing VASH2 is selected from the group consisting of pancreatic cancer, ovarian cancer, bile duct cancer, esophageal cancer, stomach cancer, colon cancer, liver cancer, gallbladder cancer, breast cancer, oral cancer, cervical cancer, endometrial cancer, renal cell cancer, bladder cancer, prostate cancer, a testicular tumor, lung cancer, skin cancer, and a brain tumor.

9. A method for inhibiting metastasis of cancer expressing VASH2, comprising administering either or both of:
   (1) a peptide including the amino acid sequence SEQ ID NO: 4; and
   (2) a peptide including the amino acid sequence of SEQ ID NO: 4 conjugated with a carrier protein; to a subject.

10. The method according to claim 9, wherein the peptide is amidated at the C-terminus.

11. The method according to claim 9, wherein the carrier protein is selected from the group consisting of bovine serum albumin (BSA), rabbit serum albumin (RSA), ovalbumin (OVA), keyhole limpet hemocyanin (KLH), OSK-1, thyroglobulin (TG), and an immunoglobulin.

12. The method according to claim 9, wherein the cancer expressing VASH2 is selected from the group consisting of pancreatic cancer, ovarian cancer, bile duct cancer, esophageal cancer, stomach cancer, colon cancer, liver cancer, gallbladder cancer, breast cancer, oral cancer, cervical cancer, endometrial cancer, renal cell cancer, bladder cancer, prostate cancer, a testicular tumor, lung cancer, skin cancer, and a brain tumor.

* * * * *